US008900189B2

(12) United States Patent
Yodfat et al.

(10) Patent No.: US 8,900,189 B2
(45) Date of Patent: Dec. 2, 2014

(54) DEVICE FOR ACCURATE INFUSION OF FLUIDS

(75) Inventors: Ofer Yodfat, Modi'in (IL); Shai Ben-David, Ramat Ishai (IL); Yair Dan, Kibutz Ein-Harod Hioud (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/384,011

(22) PCT Filed: Jul. 15, 2010

(86) PCT No.: PCT/IL2010/000566
§ 371 (c)(1),
(2), (4) Date: Apr. 3, 2012

(87) PCT Pub. No.: WO2011/007356
PCT Pub. Date: Jan. 20, 2011

(65) Prior Publication Data
US 2012/0191043 A1    Jul. 26, 2012

Related U.S. Application Data

(60) Provisional application No. 61/226,158, filed on Jul. 16, 2009.

(51) Int. Cl.
*A61M 37/00* (2006.01)
*A61M 5/142* (2006.01)
*A61M 5/145* (2006.01)

(52) U.S. Cl.
CPC ....... *A61M 5/14244* (2013.01); *A61M 2205/17* (2013.01); *A61M 5/14248* (2013.01); *A61M 2005/14533* (2013.01); *A61M 5/1452* (2013.01)
USPC .......................................... 604/155; 604/131

(58) Field of Classification Search
CPC .............. A61M 5/14566; A61M 2005/14573; A61M 5/145; A61M 5/1452; A61M 5/1456
USPC ................. 604/154, 155, 131–133, 209–211
See application file for complete search history.

(56) References Cited

U.S. PATENT DOCUMENTS

| 5,957,895 A | 9/1999 | Sage et al. |
| 5,971,963 A | 10/1999 | Choi |

(Continued)

FOREIGN PATENT DOCUMENTS

| EP | 0514907 A1 | 11/1992 |
| EP | 1759727 A1 | 3/2007 |

(Continued)

OTHER PUBLICATIONS

International Search Report for International Application No. PCT/IL2010/000566 date if mailing Dec. 28, 2010.

*Primary Examiner* — Theodore Stigell
*Assistant Examiner* — Benjamin Koo
(74) *Attorney, Agent, or Firm* — Roche Diagnostics Operations, Inc.

(57) ABSTRACT

Embodiments of the present disclosure are directed to devices, systems and methods for increasing the accuracy of delivery of a fluid/drug in a fluid/drug delivery device/system. In some embodiments, a fluid infusion device is provided for delivering a drug into the body of a user, and includes at least one housing, a reservoir, a plunger and a drive-screw, where the drive-screw includes a first end and a second end, the first end being configured to operatively connect to the plunger. The device may further include a driving mechanism comprising at least a motor and one or more gears, where the one or more gears include a rotating sleeve configured for engagement with the second end of the drive-screw, a controller for at least controlling operation of the driving mechanism, and a support casing configured to substantially support the rotating sleeve and enable substantially free rotation of the rotating sleeve therein.

16 Claims, 20 Drawing Sheets

(56) References Cited

U.S. PATENT DOCUMENTS

| | | |
|---|---|---|
| 6,248,093 B1 | 6/2001 | Moberg |
| 6,485,461 B1 | 11/2002 | Mason et al. |
| 6,589,229 B1 | 7/2003 | Connelly et al. |
| 6,723,072 B2 | 4/2004 | Flaherty et al. |
| 6,740,059 B2 | 5/2004 | Flaherty |
| 6,932,242 B2 | 8/2005 | Gerlach et al. |
| 7,390,314 B2 | 6/2008 | Stutz, Jr. et al. |
| 2003/0009133 A1 | 1/2003 | Ramey |
| 2006/0178633 A1 | 8/2006 | Garibotto et al. |
| 2006/0270987 A1* | 11/2006 | Peter .............. 604/151 |
| 2007/0010789 A1 | 1/2007 | Peter et al. |
| 2007/0106218 A1 | 5/2007 | Yodfat et al. |
| 2007/0191702 A1 | 8/2007 | Yodfat et al. |
| 2008/0215035 A1 | 9/2008 | Yodfat et al. |
| 2009/0124994 A1 | 5/2009 | Roe |
| 2010/0217230 A1 | 8/2010 | Yodfat et al. |

FOREIGN PATENT DOCUMENTS

| | | |
|---|---|---|
| EP | 2014321 A1 | 1/2009 |
| WO | WO 2007/052277 | 5/2007 |
| WO | WO 2008/012817 | 1/2008 |
| WO | WO 2009/013736 | 1/2008 |
| WO | WO 2008/078318 | 7/2008 |
| WO | WO 2008/139460 | 11/2008 |
| WO | WO 2009/016636 | 2/2009 |
| WO | WO 2009/125398 | 10/2009 |
| WO | WO-2009125398 A2 | 10/2009 |

* cited by examiner

DEVICE FOR ACCURATE INFUSION OF FLUIDS

CROSS-REFERENCE TO RELATED APPLICATION

The present application is a 35 U.S.C. §371 national stage entry of PCT/IL2010/000566, which has an international filing date of Jul. 15, 2010 and claims benefit and priority to U.S. Provisional Patent Application Ser. No. 61/226,158, filed on Jul. 16, 2009, entitled "Infusion Device with Improved Accuracy", the disclosures of which are herein incorporated by reference in their entireties.

FIELD

The present disclosure relates generally to devices, methods and systems for sustained infusion of fluids and/or analyte sensing. More particularly, the disclosure relates to devices, methods and systems that include a skin securable (e.g., adherable) unit comprising a reusable part and a disposable part. Even more particularly, the present disclosure relates to a two-part skin securable unit utilizing a movable piston pumping mechanism that delivers fluid at a high accuracy rate.

BACKGROUND OF THE DISCLOSURE

Diabetes Treatment

Medical treatment of several illnesses requires continuous drug infusion into various body compartments, such as subcutaneous and intra-venous injections. Diabetes mellitus (DM) patients, for example, require the administration of varying amounts of insulin throughout the day to control their blood glucose levels. In recent years, ambulatory portable insulin infusion pumps have emerged as a superior alternative to multiple daily syringe injections of insulin, initially for Type 1 diabetes patients and consecutively for Type 2 diabetes patients. These pumps, which deliver insulin at a continuous basal rate as well as in bolus volumes, were developed to liberate patients from repeated self-administered injections, and allow them to maintain a near-normal daily routine. Both basal and bolus volumes must be delivered in precise doses, according to individual prescription, since an overdose or under-dose of insulin could be fatal.

Generations of Insulin Pumps and Continuous Glucose Sensors

The first generation of portable insulin pumps refers to a "pager like" device with a reservoir included within a housing and long tubing is required to deliver insulin from the reservoir to the infusion site. Examples of such devices are disclosed in U.S. Pat. Nos. 6,248,093 and 7,390,314. These devices are usually heavy and bulky and the tubing substantially disturbs daily activity.

To avoid the limitations of first generation infusion pumps, an additional concept was proposed, which was implemented in second generation pumps. The additional concept concerns a remote controlled skin adherable device having a bottom surface adapted to be in contact with the patient's skin. The reservoir is contained within a housing and filled using an additional syringe. This paradigm was discussed, for example, in U.S. Pat. Nos. 5,957,895, 6,589,229, 6,740,059, 6,723,072, and 6,485,461. These second generation skin adherable devices still have several drawbacks, the most significant being that the entire device should be disposed of every 2-3 days (due to insertion site infections and reduced insulin absorption) including all the expensive components (electronics, driving mechanism, etc.).

Third generation skin-securable devices were devised to avoid the cost issues of the second generation devices and to extend patient customization. An example of such a device is described in U.S. Patent Application Publication No. 2007-0106218 and in International Patent Application Publication No. WO/2007/052277. This third generation device contains a remote control unit and a skin-securable (e.g., adherable) patch unit that include two parts: (1) a reusable part containing the electronics, at least a portion of the driving mechanism and other relatively expensive components, and (2) a disposable part containing the reservoir. A skin-securable fluid (e.g., insulin) delivery device is also disclosed in U.S. patent application Ser. No. 11/989,681 and in International Patent Application Publication No. WO/2008/012817, the disclosures of which are incorporated herein by reference in their entireties.

A fourth generation infusion device was devised as a dispensing unit that can be disconnected and reconnected to a skin-adherable cradle unit, as disclosed, for example, in U.S. Patent Application Publication No. 2008-0215035 and in International Patent Application Publication No. WO/2008/078318. Such skin-securable dispensing units can be operated using a remote control and/or a user interface (e.g., a button-based interface) provided on a housing of the dispensing unit, as disclosed, for example, in International Patent Application Publication No. WO/2009/013736, filed Jul. 20, 2008, claiming priority to U.S. Provisional Patent Application No. 60/961,527, and entitled "Manually Operable Portable Infusion Device", and in International Patent Application Publication No. WO/2009/016636, filed Jul. 31, 2008, claiming priority to U.S. Provisional Application Ser. Nos. 60/963,148 and 61/004,019, and entitled "Portable Infusion Device Provided with Means for Monitoring and Controlling Fluid Delivery", the disclosures of which are incorporated herein by reference in their entireties.

The third and fourth generation dispensing patches can be incorporated with an analyte (i.e. glucose) sensing apparatus enabling continuous readings of analyte levels. Fluid dispensing can be done automatically according to analyte sensing (closed loop system) or semi automatic if the user wishes to control delivery (open loop system). Such dual function sensing and dispensing devices are disclosed, for example, in U.S. Patent Application Publication No. 2007-0191702, the disclosure of which is incorporated herein by reference in its entirety.

Pump Gears and Transmission Error

The pumping mechanism employed in most insulin pumps is a "syringe-like mechanism", known also as a positive displacement piston pump. In such a pump, a plunger (piston) moves (i.e., slides) within a cylindrical shaped barrel (reservoir), pushing the contents (i.e., drug) out, typically, through a small opening at the end of the reservoir/syringe. The plunger is pushed forward by a drive-screw (plunger rod) that can be integral, rigidly connected, or articulated with the plunger head (piston). The driving mechanism typically consists of a motor and a transmission gear system, which is used to linearly displace the drive-screw either by rotation of the drive-screw, rotation of a drive nut, or rotation of a drive pinion over a rack that serves as a drive-screw (a rack is a toothed bar or rod. Torque is converted to linear force by meshing a rack with a pinion: the pinion turns; the rack moves in a straight line). The transmission gear system is used for reduction of motor revolutions and/or for changing the rotation axis by 90 or 180 degrees, for example.

Typically, the pump's transmission gear system consists of two or more parallel shaft gears (e.g., single stage reduction), comprising two metal cogwheels, integrated with a tooth mesh and both cogwheel shafts are parallel mounted on a metal chassis (gear casing).

Transmission error (hereinafter referred to also as "TE") is defined as the difference between the actual position of the output gear and the position it would occupy if the gear drive were perfectly conjugated. The equation for TE is expressed as:

$$TE = \theta_2 - \left(\frac{Z_1}{Z_2}\right)\theta_1$$

Where $Z_1$ is the number of teeth of the input gear, $Z_2$ is the number of teeth of the output gear and $\theta_1$ and $\theta_2$ denote the angular position of the input and output gears in radians, respectively. Essentially, TE is the difference between the actual position of the output shaft of a gear drive and the position that the output shaft of the gear drive would have if the gear drive were perfect, without errors or deflections. The main contributors to transmission error are geometrical errors in alignment (e.g., due to assembly errors/tolerances), tooth profile (e.g., due to manufacturing imperfections/tolerances), elastic deformation of local contacts, and the deflection of the gear shafts and casing due to the transmitted load through and transverse to the gear rotation axis. Depending on its cause, the frequency of the transmission error may be high (i.e., >1 per cycle of the output shaft), or it may be substantially equal to the frequency of the output shaft's rotation (i.e., =1 per cycle of the output shaft). The magnitude of this one per cycle error may depend on load and it may thus be classified as loaded TE.

A consequence of TE existing in transmission gear systems of insulin pumps is inaccuracy in drug delivery. Insulin pumps should deliver basal doses at a very low rate along the entire day with high precision (e.g., 0.05 U/h that is 5 mm$^3$/h in case of 100 U/ml rapid acting insulin). Typically, the existence of TE introduces a "sine like" wave to the expected drug delivery linear curve with fluctuations that can substantially affect insulin delivery accuracy and threaten the life of the diabetes patient.

It is understood that TE is may be minimized in gear systems of 1st generation pumps by making gears, gear casings, and bearings robust (e.g., relatively large components, metal components). Consequently these "pager like" pumps are undesirably heavy, bulky, and expensive.

The design goal of skin securable 2nd, 3rd, and 4th generation pumps, however, is that they be small and lightweight, with minimal components and assembly costs. Consequently, the gears, gear casing, and bearings for these pumps are configured to be miniature and lightweight and therefore, they are typically made of plastic (i.e., polycarbonate, polypropylene, etc.). These plastic parts should maintain metal parts' requirements and avoid (or minimize) transmission error. However, plastic parts, especially miniature plastic parts, are typically more subject to manufacturing (e.g., injection molding) and assembly imperfections than metal parts, and are also typically more subject to deformations caused by forces/load applied during routine operation of the pump, all of which are likely to result in transmission error. Transmission error may further be aggravated in 3rd and 4th generation two-part skin securable pumps because the interface between the drive-screw (piston rod) and gear is achieved during connection of the two parts by the user, thus increasing the risk of component misalignment, for example.

Thus, it is desirable to provide a skin securable drug dispensing patch unit which is miniature, discreet, economical for the users and highly cost effective. The patch unit includes a driving mechanism comprising a motor and a gear system with minimized transmission error, for delivering fluids at a high accuracy rate.

It is also desirable to provide a skin securable drug dispensing patch unit that includes two parts, e.g., a reusable part and a disposable part. The disposable part ("DP") includes a reservoir and a slidable plunger. The reusable part ("RP") includes electronics, and at least a portion of a driving mechanism including a motor and a gear system with minimized transmission error, for delivering fluids at a high accuracy rate.

SUMMARY

Embodiments of the current disclosure are directed to devices, methods and systems that deliver therapeutic fluid into the body. Some such embodiments may include a syringe type pumping mechanism comprising a barrel reservoir (hereinafter "reservoir" or "barrel") and a movable/slidable plunger (e.g., piston and gaskets) that moves in a first direction (e.g., forwardly to push fluid out of the reservoir) upon linear movement of a rotating drive-screw. In some embodiments, the drive-screw has a distal end that articulates with the plunger and a proximal end (hereinafter "drive-screw rotator" or "engagement member") that includes longitudinal ridges (or "teeth") for engagement with the driving mechanism. In some embodiments, the drive-screw rotator may be substantially cone shaped. The driving mechanism may be comprised of a motor and a transmission/reduction gear system (i.e., a gear system which may function to transmit and/or reduce speed) that rotates the drive-screw.

The gear system may comprise a planetary reduction unit and one or more additional gears. The last gear of the gear system may be configured as a long tube (e.g., cylinder) with external teeth for engagement with an adjacent gear of the gear system and one or more internal teeth for engagement with the drive-screw rotator (this last gear may be referred to hereinafter as "rotating sleeve" or "receiving member"). The length of the rotating sleeve may substantially correspond to the length of the drive screw, or it may be shorter/longer. The rotating sleeve may rotate within a casing that may comprise one or more V-blocks/V-grooves (e.g., front and rear of the casing, in other words, spaced apart along the casing) within the interior of the casing and a supporting spring (or any other biasing element) that forces the rotating sleeve against or adjacent the V-blocks walls. In some embodiments, after engagement of the drive-screw rotator and the rotating sleeve, and upon motor activation, the rotating sleeve rotates the drive-screw rotator.

In some embodiments, the device comprises at least the following three (3) components: a two-part dispensing patch unit (hereinafter "patch unit" or "dispensing unit"), a skin adherable cradle unit (hereinafter "cradle") and a remote control unit (hereinafter "remote control" or "RC"). In some embodiments, the patch unit can be disconnected and reconnected from and to the cradle. A connecting lumen in the patch unit provides fluid communication between the patch unit and a subcutaneous cannula that is rigidly connected to the cradle. Fluid delivery can be remotely controlled using the RC or using manual buttons/switches located on the patch.

Below is a description of examples of each unit, according to some embodiments:

1—Patch: comprises a pumping mechanism, reservoir and exit port. The patch can be configured as a single part including the reservoir, one or more batteries, electronics, and pumping mechanism or as a two-part unit that comprises:

- a. Reusable Part (hereinafter "RP")—includes motor, gear/s, electronics, and other relatively expensive components. In some embodiments, the RP may be a durable unit/assembly which is replaced every three months, for example.
- b. Disposable Part (hereinafter "DP")—includes an exit port, a barrel (reservoir), a plunger, a drive-screw, and a nut. In some embodiments the DP further includes one or more batteries. In some embodiments, the reservoir may include a flat configuration (e.g., oval, ellipse, four arches, etc.) maintaining a thin DP profile. In some embodiments, the DP may be a single-use unit/assembly which is replaced every two-three days, for example.

In some embodiments, each of the RP and DP include a housing (shell, or pocket) and an insert (chassis) and upon RP-DP connection the housings and/or inserts are coupled together.

2—Cradle: a typically flat sheet (or plate) having an adhesive layer facing the skin. The cradle may be provided with a passageway to a subcutaneous cannula, and configured for secure connection with the cannula and with the patch.

3—RC: a handheld unit micro-processor based device for programming fluid flows, controlling the patch, data acquisition, and providing indications (e.g., via a display). In some embodiments, the RC may comprise a wrist-watch, cellular phone, PDA, iPhone, iPod, and laptop (and the like).

Thus, it is an object of some of the embodiments of the present disclosure to provide a device/system for medical infusion of fluids into the body that includes a syringe type pumping mechanism and a driving mechanism that comprises a transmission/reduction gear that rotates a drive-screw with minimal transmission error.

It is another object of some of the embodiments of the disclosure to provide an infusion device/system that includes a two-part skin securable patch comprising a reusable part and disposable part. The reusable part includes one or more or all of a motor, gear(s), electronics, and other relatively expensive components and the disposable part includes one or more or all of an exit port, a reservoir, a plunger, and a drive-screw. One or more batteries may reside in the disposable part and/or in the reusable part.

It is another object of some of the embodiments of the disclosure to provide a skin securable patch for sustained medical infusion with controlled rate injection of a fluid into a body.

In some embodiments, a fluid delivery system for delivering a drug into the body of a user is provided. The system may comprise a fluid delivery device which includes a disposable part and a reusable part. The disposable part may comprise a disposable part housing, a reservoir containing the drug, a plunger for displacing the drug from the reservoir to the user and a drive-screw that includes a first end and a second end, the first end being configured to connect to the plunger. In some embodiments, the drive-screw may comprise at least a portion of the driving mechanism. The reusable part may comprise a reusable part housing, at least a portion of a driving mechanism which includes at least a motor and one or more gears, the one or more gears including a rotating sleeve configured to receive the second end of the drive-screw upon connection of the disposable part and the reusable part, a controller for at least controlling operation of the at least a portion of the driving mechanism, and a support casing configured to substantially support the rotating sleeve and enable substantially free rotation of the rotating sleeve therein. The system may further comprise a remote control for at least one of initiating drug delivery, programming the device, acquiring data and communicating with other electronic devices. The system may further comprise a skin securable cradle to hold the device to the skin of the user during use.

In some embodiments, a fluid infusion device for delivering a drug into the body of a user is provided and may include at least one housing, a reservoir for containing the drug, a plunger for displacing the drug from the reservoir to the user, and a drive-screw including a first end and a second end. The first end of the drive screw, in some embodiments, is configured to operatively connect to the plunger. The device may also include a driving mechanism comprising at least a motor and one or more gears, where the one or more gears include a rotating sleeve configured to engage with the second end of the drive-screw, a controller for at least controlling operation of the driving mechanism, and a support casing substantially contained within the housing. In some embodiments, the casing is configured to substantially support the rotating sleeve and enable substantially free rotation of the rotating sleeve therein.

In some embodiments, the relationship between the plunger and the first end of the drive-screw which transfers force and/or motion to the plunger may also be referred to as being configured for operative connection and/or being an operative connection (e.g., "operatively connect", "operatively connected", "operative connection"). For example: in some embodiments, such "operative connection" (and the like), may refer to the first end of the drive-screw and the plunger being an integral unit—e.g., being manufactured in one piece; and in some embodiments, operative connection may connote separate elements which are connected, either directly or via one or more other elements.

In some embodiments, the support casing noted above may be further configured to maintain a rotation axis of the rotating sleeve substantially parallel to a rotation axis of at least one other gear of the one of more gears.

In some embodiments, the support casing may be further configured to maintain proper alignment between the rotating sleeve and at least one other gear of the one of more gears. Proper alignment may comprise one or more of substantially parallel positioning and substantially accurate spacing between the rotating sleeve and the at least one other gear of the one of more gears.

In some embodiments, the device as noted above may further comprise a chassis for supporting at least a portion of the driving mechanism and the support casing. The support casing may be integral with the chassis. Moreover, in some embodiments, an interior of the casing may comprise at least one pair of substantially flat surfaces positioned adjacent one another, wherein the surfaces may be positioned relative to one another at an angle less than 180 degrees, less than about 120 degrees, and/or between about 30 degrees and about 120 degrees. In some embodiments, the at least one pair of substantially flat surfaces forms a V-block (or "V-groove").

In some embodiments, the casing comprises an interior with a shape substantially corresponding to an exterior shape of the rotating sleeve. In some embodiments, the interior includes a predetermined tolerance for enabling substantially free rotation of the rotating sleeve therein.

In some embodiments, the device according to any of the above embodiments may further comprise a biasing member for biasing the rotating sleeve relative to the casing. The biasing member may be used to bias the rotating sleeve relative to the at least one pair of substantially flat surfaces. In some embodiments, the biasing member may comprise a spring.

In some embodiments, the casing may comprise at least a pair of structural supports spaced apart from one another so as to substantially support the length of the rotating sleeve, where each support may include an interior surface which substantially corresponds to a portion of the exterior surface of the rotating sleeve. In some embodiments, at least one of the supports may comprise a substantially annular configuration.

In some embodiments, the casing includes one or more slots for receiving at least a portion of the biasing member (e.g., spring).

In some embodiments, the rotating sleeve, and optionally at least one of chassis and the casing, includes at least one opening to enable monitoring of the position of at least one of the drive-screw and the second end thereof within the rotating sleeve.

In some embodiments, the chassis includes a plurality of alignment surfaces configured to maintain at least one of substantially parallel alignment and substantially accurate spacing between at least two of a rotation axis of the motor, a rotation axis of the one or more gears and a rotation axis of the rotating sleeve. The one or more gears may include a gearbox. The device may further comprise at least one of a latching mechanism and an adhesive configured to maintain contact between the gearbox and one or more of the alignment surfaces. The gearbox may include one or more elastic portions. Upon the one or more elastic portions being forced against the chassis, the gearbox is forced against one or more of the alignment surfaces.

In some embodiments, the one or more gears may include or comprise a planetary gear unit.

In some embodiments, connection between the first end of the drive-screw of the device and the plunger may be an articulated connection.

In some embodiments, the connection between the first end of the drive-screw and the plunger preferably enables substantially free rotation of the first end within the plunger, with rotation of the drive-screw causing, or otherwise resulting in, displacement of the plunger in a linear direction within the reservoir.

In some embodiments, the second end of the drive-screw may be integral with the drive-screw. In other embodiments, the second end of the drive-screw may comprise a member which is separate from the drive-screw and is configured to be assembled with the drive-screw.

In some embodiments, the rotating sleeve of the device may include a plurality of internal grooves and/or teeth extending along at least a portion of the length of the rotating sleeve.

In some embodiments, the second end of the drive-screw of the device may include a plurality of teeth configured to engage with the internal grooves and/or teeth of the rotating sleeve.

In some embodiments, the second end of the drive-screw may further include a plurality of centralizing surfaces between adjacent teeth. The centralizing surfaces may be configured to substantially align the second end with the internal grooves and/or teeth of the rotating sleeve.

In some embodiments, at least one tooth of the plurality of teeth of the second end includes a size and/or shape which is partial to the size and/or shape of the remaining teeth.

In some embodiments, at least a portion of at least one tooth of the plurality of teeth of the second end may be elastic.

In some embodiments, the support casing may be further configured to maintain alignment between a rotation axis of the rotating sleeve and a longitudinal axis (e.g., rotation axis) of the drive screw.

In some embodiments, the following additional features may be included with devices, systems and methods according to the present disclosure as set out above or anywhere herein:
  the rotating sleeve comprises a substantially cylindrical configuration;
  the at least one housing comprises a first housing comprising a reusable part of the device and a second housing comprising a disposable part of the device, and where the reusable part and the disposable part are connectable to each other;
  the reusable part may comprise at least the controller, the support casing and at least a portion of the driving mechanism including the rotating sleeve;
  the disposable part may comprise at least the reservoir and the plunger;
  the disposable part may further comprise the drive-screw, and upon connection between the reusable part and the disposable part, the second end of the drive-screw is received within the rotating sleeve;
  connection of the reusable part and the disposable part may be configured to enable substantial proper alignment between the rotating sleeve and the second end of the drive-screw;
  a remote control for at least one of initiating drug delivery, programming the device, acquiring data and communicating with other electronic devices;
  a skin securable cradle to hold the at least one housing to the skin of the user during use; and
  at least one of a lubricant and low-friction casing material.

In some embodiments, a fluid infusion device for delivering a drug into the body of a user is provided and may include a disposable part comprising a disposable part housing, a reservoir for containing the drug, a plunger for displacing the drug from the reservoir to the user, and a drive-screw including a first end and a second end, the first end being configured to connect to the plunger. The device may also include a reusable part comprising a reusable part housing, at least a portion of a driving mechanism including at least a motor and one or more gears, where the one or more gears include a rotating sleeve configured to receive the second end of the drive-screw upon connection of the disposable part and the reusable part, a controller for at least controlling operation of the at least a portion of the driving mechanism, and a support casing configured to substantially support the rotating sleeve and enable substantially free rotation of the rotating sleeve therein. The reusable part may further comprise a reusable part chassis contained within the reusable part housing for supporting at least a portion of the driving mechanism and the support casing. Moreover, in some embodiments, the support casing may be integral with the reusable part chassis.

One of skill in the art will appreciate that the term "adjacent", according to some embodiments, can describe a relationship among two or more different items/members, as touching, or as being in close proximity but spaced apart (i.e, the items described and/or claimed as being adjacent may or may not touch one another).

It is worth noting, that features described in any one or another of the embodiments described above and in the detailed description of disclosure which follows, may be combined, mixed and/or matched with one or another of the disclosed embodiments, and included features thereof.

BRIEF DESCRIPTION OF THE DRAWINGS

Some of the embodiments of the present disclosure are described with reference to the accompanying drawings. In the drawings, like reference numbers indicate identical or functionally similar elements.

DETAILED DESCRIPTION

Figure 1:
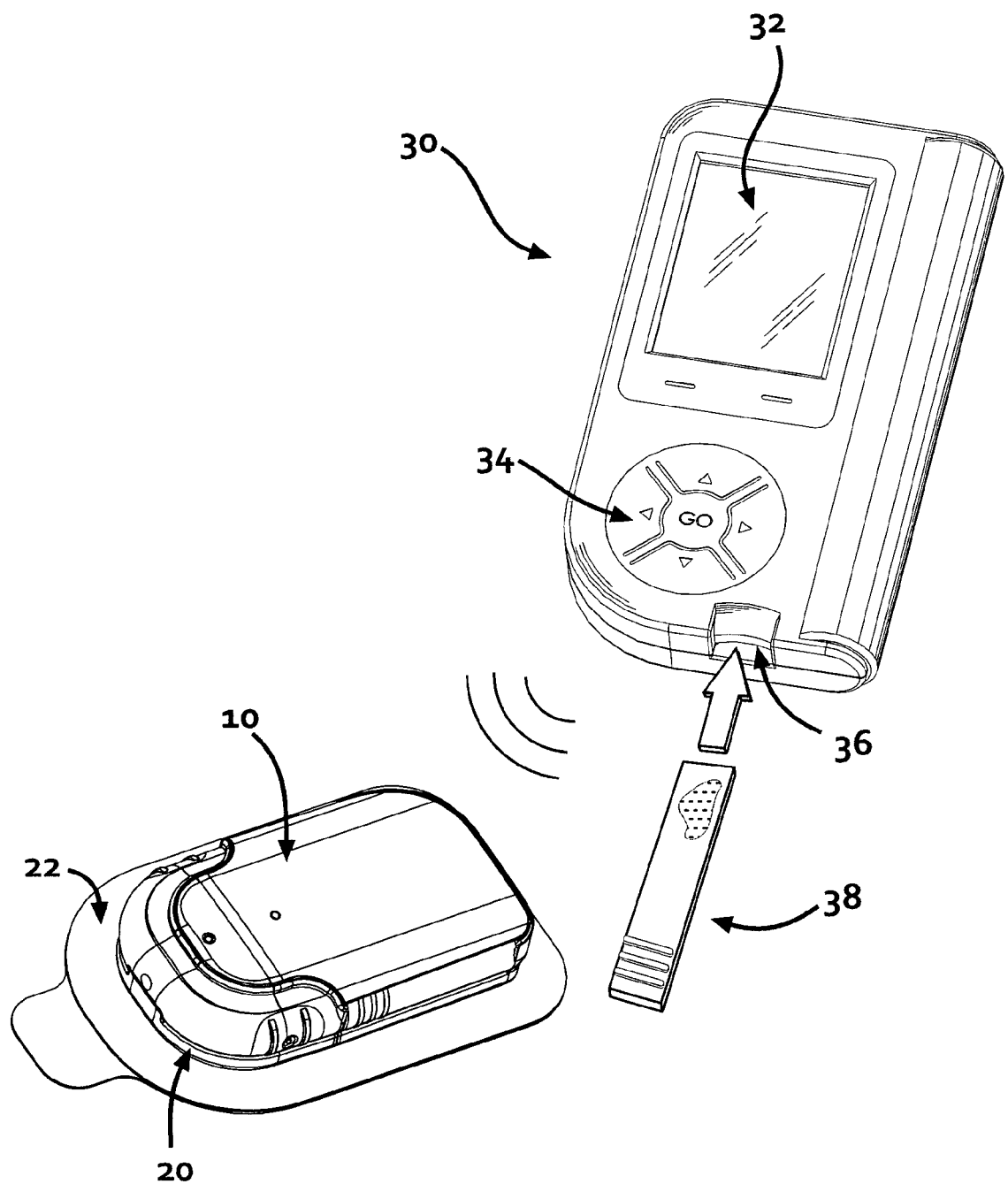
FIG. 1 shows a system comprising three units: a remote control unit, which may include an integrated blood glucose monitor, a two-part skin securable dispensing patch unit, and a skin adherable cradle unit, according to some embodiments.

FIG. 1 shows a system, according to some embodiments, that may include (at least) the following three (3) components:

Dispensing patch unit 10 ("patch") for delivery of therapeutic fluid/s to a patient. The patch 10 may be comprised of one or two parts (e.g., a reusable part and a disposable part). In some embodiments, the patch 10 may be disconnected from and reconnected to a skin securable (e.g., adherable) cradle unit 20 ("cradle"). Commands relating to fluid dispensing may be provided, according to some embodiments, via a remote control and/or using buttons/switches located on the patch 10, as disclosed, for example, in International Patent Application Publication No. WO/2009/013736, and International Patent Application Publication No. WO/2009/016636, the contents of all of which are hereby incorporated by reference in their entireties.

Remote control unit 30 ("remote control"), which may include, in some embodiments, an integrated blood glucose monitor, may also be provided. The remote control 30 may include a screen 32, a keypad 34, and a slot 36 to receive a blood test strip 38. The remote control 30 may be used for patch programming and/or data acquisition, and may also be used for communicating with other electronic devices such as a personal computer ("PC"), to carry out, for example, data downloading and uploading. In some embodiments, the remote control 30 may be configured, without limitation, as a wrist-watch, a cellular phone, a personal digital assistant, iPhone, iPod, or an mp3 player.

Embodiments of the cradle 20 may be configured as a generally flat sheet or plate having a surface that is securable (e.g., adherable) to the skin of a patient, e.g., via an adhesive layer 22 provided on a bottom surface of the cradle 20. The cradle 20 may also contain a passageway for insertion of a cannula (not shown) into the body. In some embodiments, the cradle 20 may further include connecting means/connectors (e.g., snaps) to rigidly secure the patch 10 and/or cannula to the cradle 20, as well as ribs, walls, and the like, so as to maintain structural rigidity.

Examples of such a device are disclosed in U.S. Patent Application Publication No. 2008-0215035, International Patent Application Publication No. WO/2008/078318, U.S. Patent Application Publication No. 2007-0106218, International Patent Application Publication No. WO/2007/052277, and International Patent Application Publication No. WO/2009/125398, the contents of all of which are hereby incorporated by reference in their entireties.

U.S. Patent Application Publication No. 2007-0191702, the content of which is hereby incorporated by reference in its entirety, discloses a device that includes a dispensing patch unit (e.g., an insulin dispensing patch) and an analyte sensor (e.g., a continuous glucose monitor). This type of dual function device may have a similar configuration to that outlined above and may also be disconnected from and reconnected to the skin at the patient's discretion.

Figure 2A:
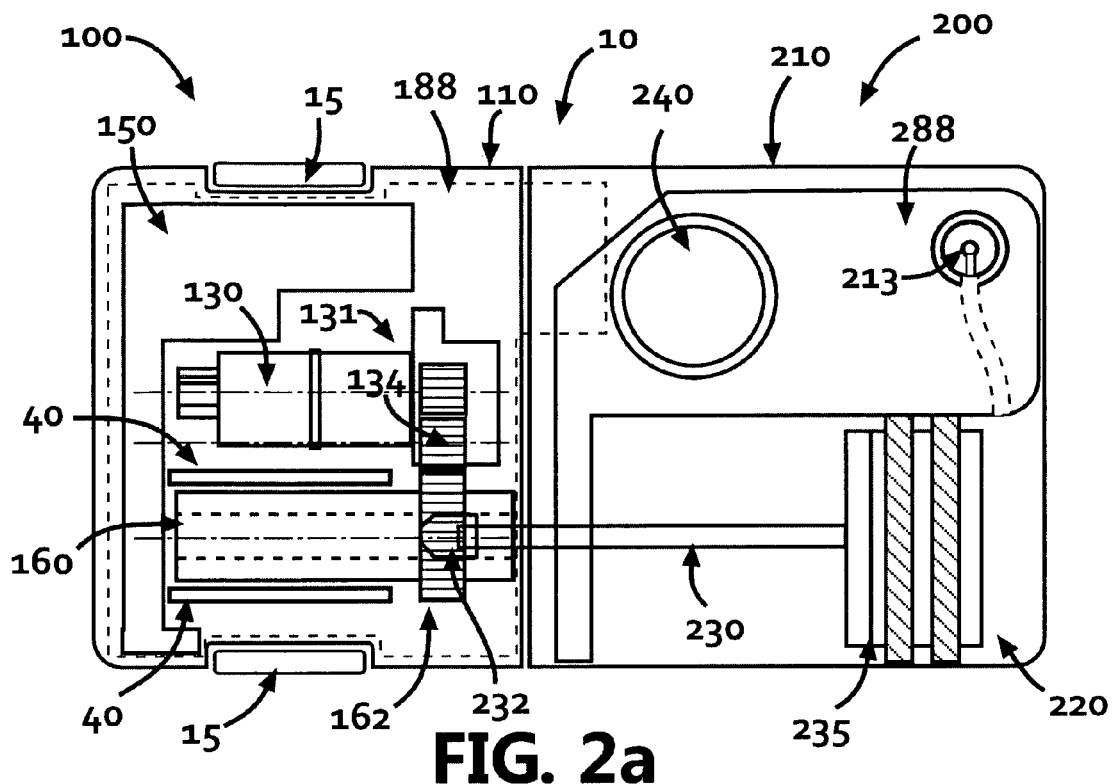
FIGS. 2a-2b show a cross sectional view of the connected (FIG. 2a) and disconnected (FIG. 2b) two part skin securable patch unit, according to some embodiments.
Figure 2B:
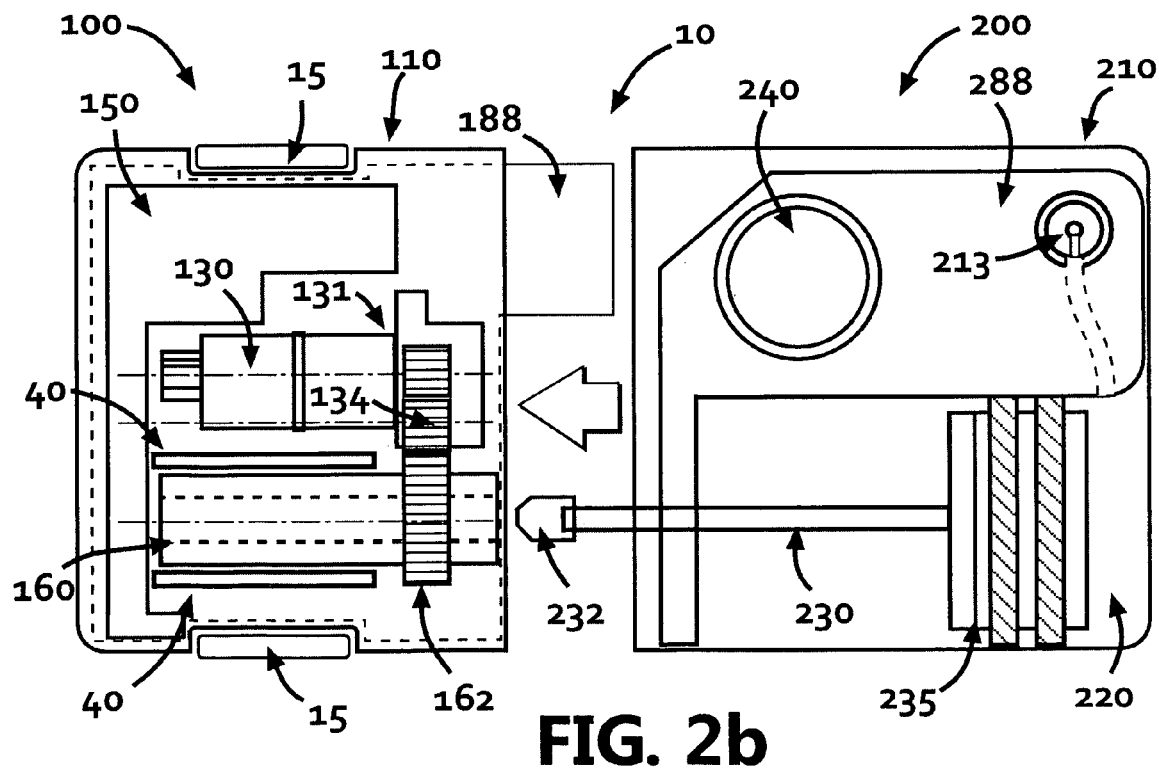

FIGS. 2a-2b show longitudinal cross sectional views of a two-part dispensing patch unit 10, according to some embodiments. FIG. 2a shows the two parts connected, and FIG. 2b shows the two parts disconnected. In some embodiments, the dispensing patch unit 10 may include a disposable part 200 ("DP") and a reusable part 100 ("RP"). In some embodiments, the RP 100 may be a durable unit/assembly which is replaced every three months, for example, and the DP 200 may be a single-use unit/assembly which is discarded and replaced every 2-3 days, for example. In other words, a single RP 100 may be coupled to approximately thirty (or more) different DPs 200 throughout its lifetime. The disposable part 200 may include an external housing 210, a portion of which may also form/define the reservoir 220, and a chassis (insert) 288 to support DP components including, for example, a battery 240 and an outlet port 213. A plunger (piston) 235 may be linearly displaced within the reservoir 220 by a drive-screw (plunger rod) 230, that may be integral with the plunger 235 or connected/coupled to the plunger 235 via a distal end of the drive-screw. The drive screw (plunger rod) 230 may further include a proximal end configured as a drive-screw rotator 232. The drive-screw rotator 232 may be integral with the drive-screw 230 or attached (e.g., glued) to the drive-screw 230. The reusable part 100 may include an external housing 110, and a chassis (insert) 188 to support the RP components including, for example, electronics 150 (e.g., attached to a PCB) and at least a portion of a driving mechanism. The driving mechanism may include a motor 130 and a transmission/reduction gear system. Such gear system may include a gearbox 131, which may comprise a planetary unit. The term "gearbox" may be used hereinafter to describe either a shell/housing with at least one gear enclosed therein, or the shell/housing alone. In some embodiments, the gear system may further include one or more additional gears, e.g., gear 162, which meshes with one or more gears of the gearbox, e.g., gear 134. Gear 162 may be coupled to, or integral with, a rotating sleeve 160 for engagement with the drive-screw rotator 232 of the DP 200. During DP-RP connection, in some embodiments, the drive-screw rotator 232 is received by the rotating sleeve 160. The rotating sleeve 160 may be enclosed within a casing 40 configured to support the rotating sleeve 160 and maintain alignment of the rotating sleeve 160 and the rotating sleeve gear 162 with the longitudinal axis of the device and/or with the longitudinal axis (e.g., the axis of rotation) of a component of the device (e.g., gear 134). The casing 40 may be part of the RP chassis 188 or it may be a separate component/structure. In some embodiments, the casing 40 may include one or more pieces attachable to (e.g., using glue or ultrasonic welding), or integral with, the RP chassis 188. Two operating buttons 15 (e.g., bolus buttons) may be provided on the RP housing 110 for issuing commands related to fluid delivery, for example.

Figure 3:
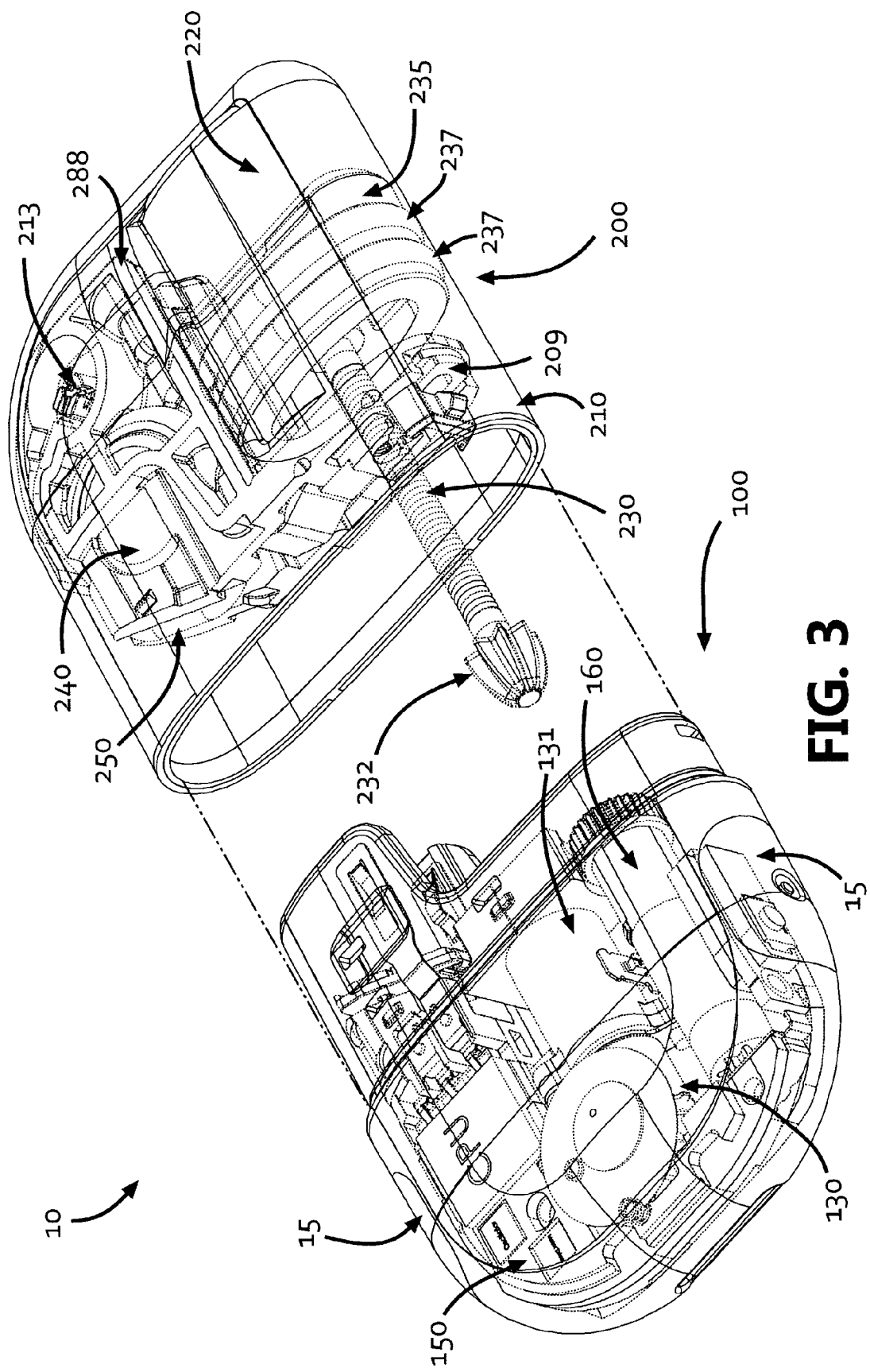
FIG. 3 shows a perspective view of a disconnected two-part dispensing unit that comprises a reusable part and a disposable part, according to some embodiments.

FIG. 3 shows a further embodiment of a patch 10 comprised of two parts—a reusable part 100 and a disposable part 200. The reusable and disposable parts may each be comprised of one or more housings (interchangeably wording with "shell" or "pocket") and chassis (interchangeably wording with "insert"). The chassis may be used as a support structure ("skeleton") for attachment of components within the housing. The pumping mechanism may be "syringe-like" and may include a sliding plunger 235 within a barrel (i.e., a reservoir) 220, which may be cylindrical or oval, for example. The RP 100 may include the relatively expensive components including (but not limited to) a motor 130, gear system including a gearbox 131 and rotating sleeve 160, electronics 150, and operating buttons 15, e.g., to manually deliver fluid without the aid of the remote control (also referred-to as "bolus buttons"). The DP 200 may include the reservoir 220, the plunger 235 with one or more gaskets 237, a threaded plunger rod ("drive-screw") 230 that may have a distal end articulating with the plunger 235 and a proximal end that is engaged with the rotating sleeve 160 after RP-DP connection. The proximal end may be configured as a drive-screw rotator 232 (or "engagement member"). The DP 200 may further include an engagement nut 209 (hereinafter "nut"), an exit port 213 and, in some embodiments, one or more batteries 240. The DP exit port 213 may include a connecting lumen (not shown) that, in some embodiments, maintains fluid communication between the reservoir 220 and the body, e.g., via a cannula (not shown) inserted in the subcutaneous tissue. A delivery tube 250 may be used to connect the reservoir 220 to the connecting lumen. Forward motion of the plunger 235 urges fluid from the reservoir 220 into the delivery tube 250. In some embodiments, the reservoir's cross-section is oval/elliptical, or it may include a plurality of arches (e.g., four or eight arches) to maintain a thin profile of the patch. The DP 200 includes a shell (pocket) 210 to house internal components. A portion of the DP shell 210 may also define the reservoir 220 (i.e., serve as one or more walls of the reservoir 220). The DP "insert" 288, in some embodiments, supports at least one of and preferably all of the delivery tube 250, connecting lumen and one or more batteries 240, and it may also serve as a construction reinforcing means.

Figure 4:
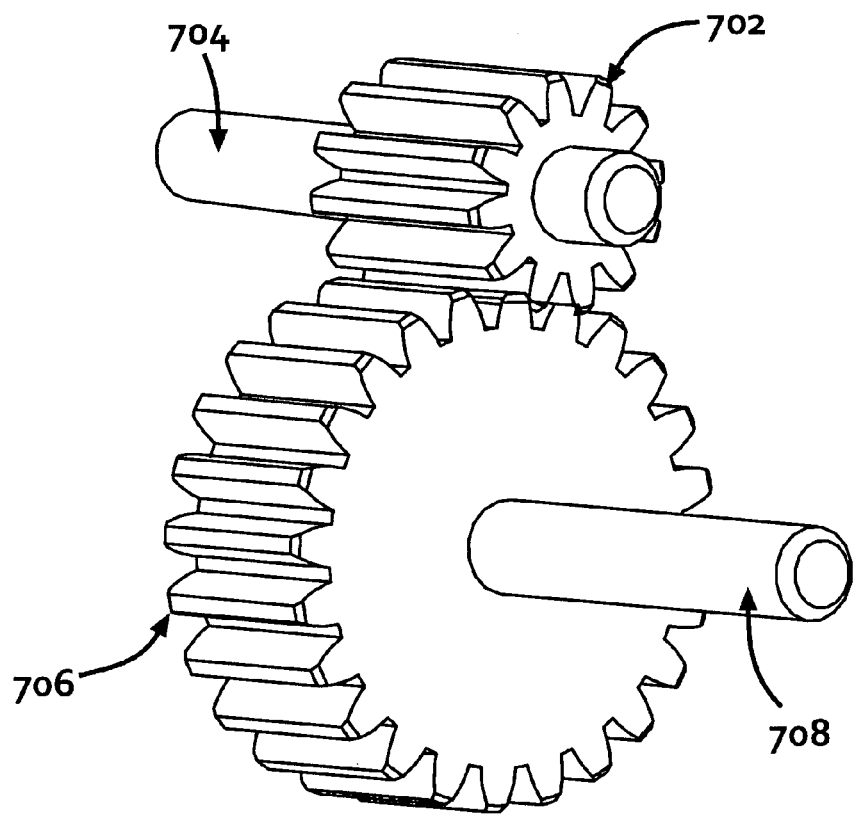
FIG. 4 shows a typical one stage reduction gear system, according to some embodiments.

FIG. 4 shows a transmission/reduction gear system, according to some embodiments, that comprises two intermeshing cogwheels (gears) 702 and 706 and shafts 704 and 708. In this example, rotation of the input shaft 704 and the input gear 702 causes rotation of the output gear 706 and the output shaft 708 at a slower rate (i.e., when the smaller gear 702 has completed one revolution the larger gear 706 will have completed less than one revolution).

Figure 5:
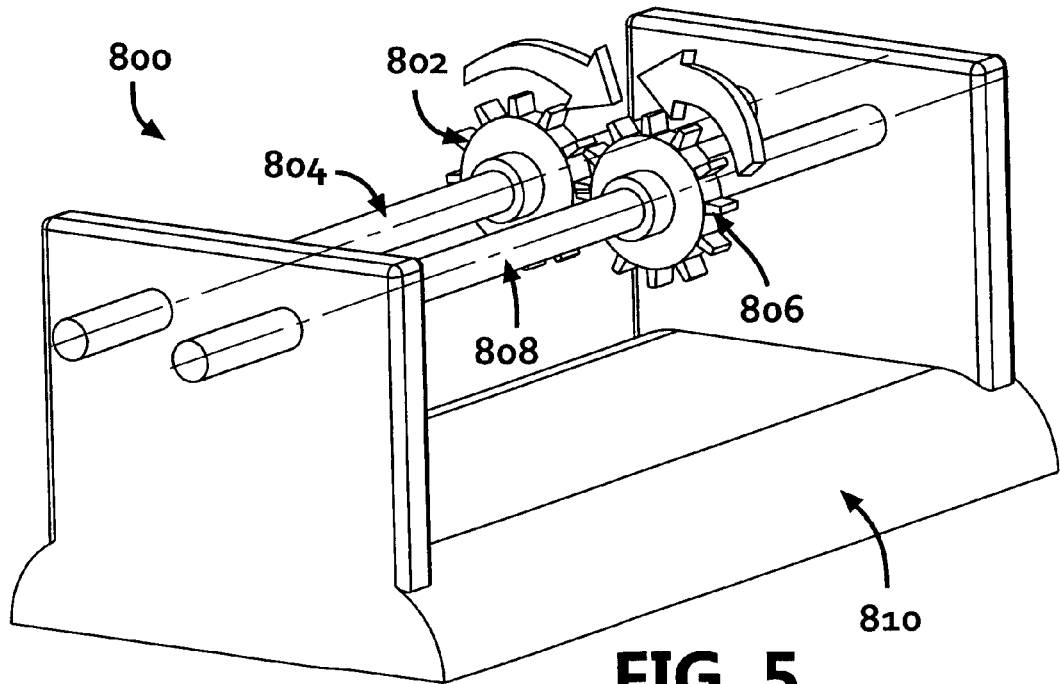
FIG. 5 shows a transmission gear system. Two intermeshing cogwheels are mounted on two parallel shafts that are aligned by a rigid casing, according to some embodiments.

FIG. 5 shows a transmission/reduction gear system 800, according to some embodiments, that comprises two intermeshing cogwheels (gears) 802 and 806 mounted on shafts 804 and 808, respectively. In this example, the intermeshing cogwheels 802 and 806 have the same number of teeth, and the shafts 804 and 808 are parallel to each other, which may be established by a casing (housing) 810. In this situation, and according to some embodiments, rotation of one shaft (the input shaft) will result in equal rotation of the other shaft (output shaft). Free rotation of the shafts within the casing may be maintained by bearings (not shown) or lubrication means (i.e., greasing), for example.

Figure 6A:
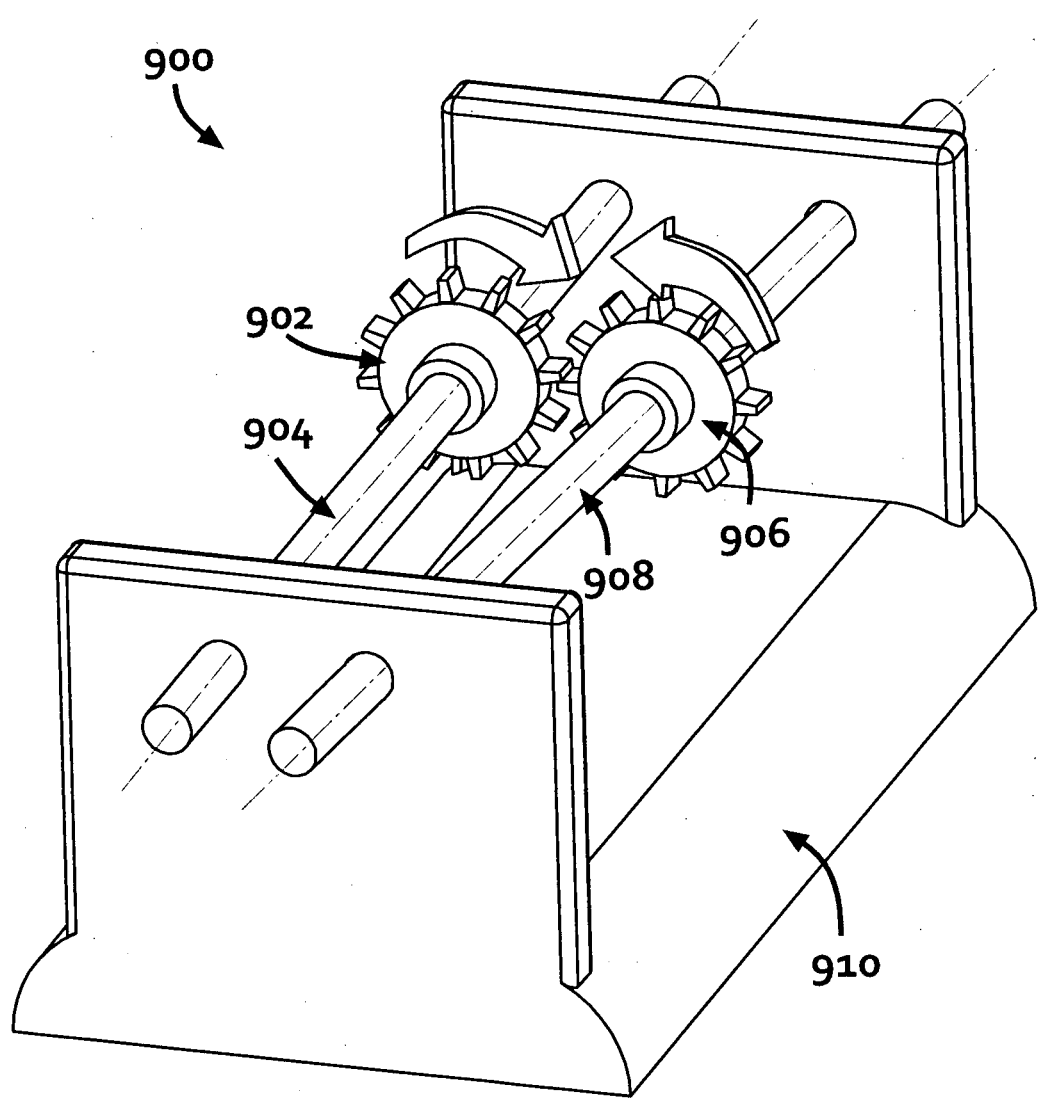
FIGS. 6a-6c show a transmission gear system. Two intermeshing cogwheels are mounted on two non-parallel shafts, according to some embodiments.

FIG. 6a shows a transmission/reduction gear system 900, according to some embodiments, that comprises two intermeshing cogwheels (gears) 902 and 906 mounted on shafts 904 and 908, respectively. In this example, the intermeshing cogwheels 902 and 906 have the same number of teeth, however casing 910 does not maintain the shafts 904 and 908 parallel to each other. In this situation, and according to some embodiments, rotation of one shaft (input shaft) will not result in equal rotation of the other shaft (output shaft), i.e., transmission error exists.

Figure 6C:
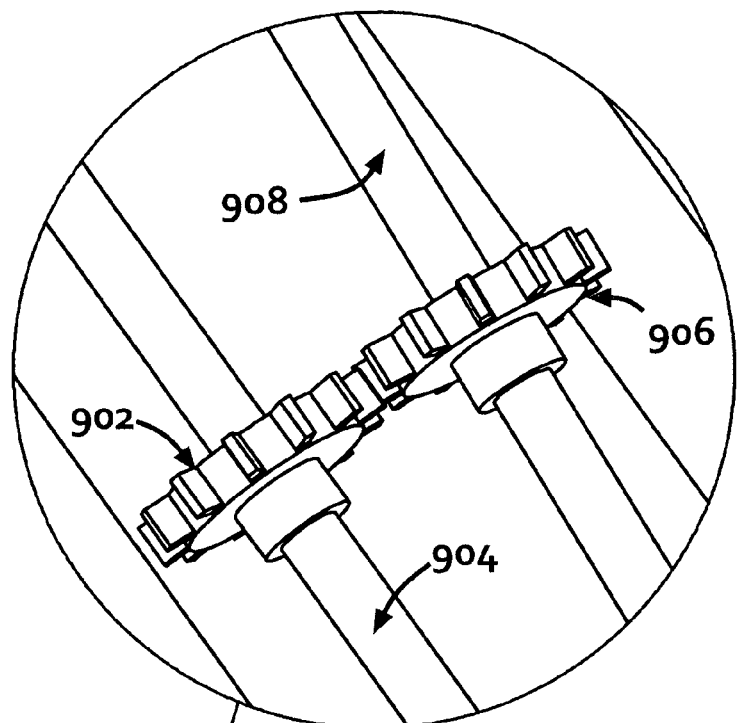
Figure 6B:
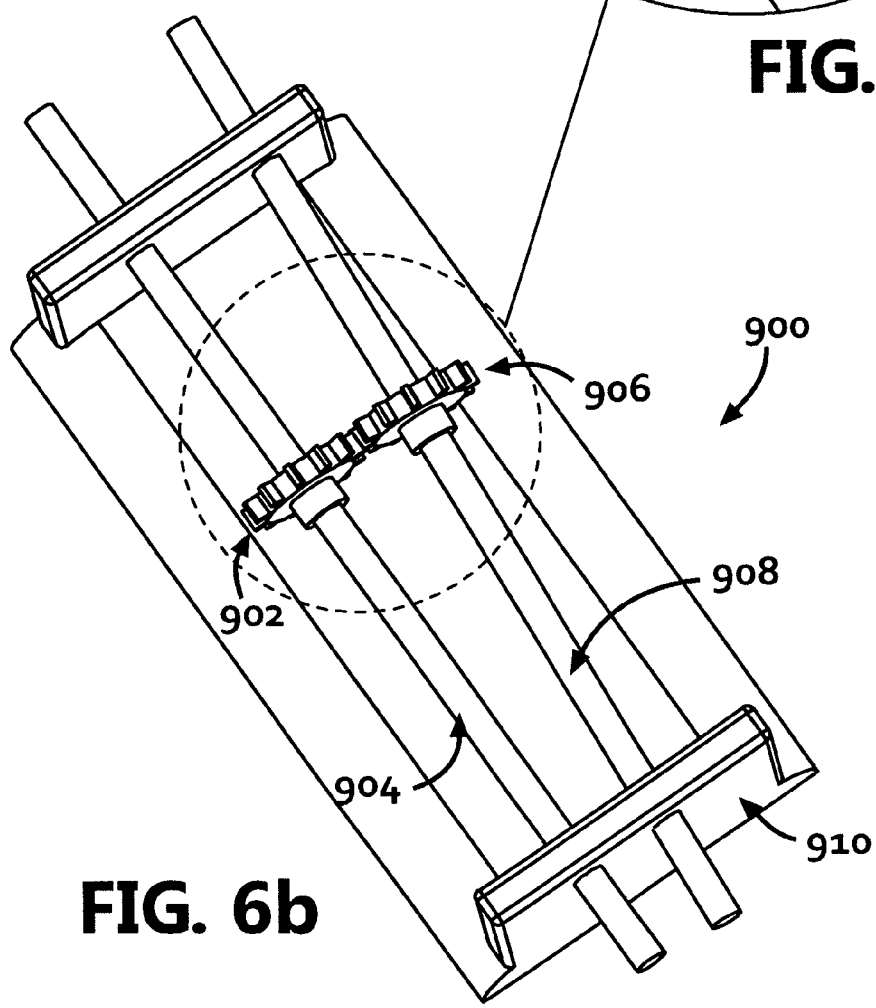
Figure 7A:
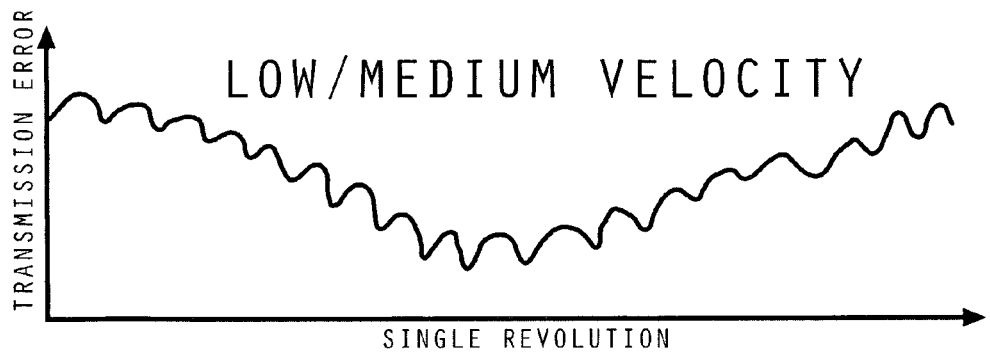
FIGS. 7a-7d show representing graphs of transmission error at various rotational velocities, according to some embodiments.
Figure 7B:
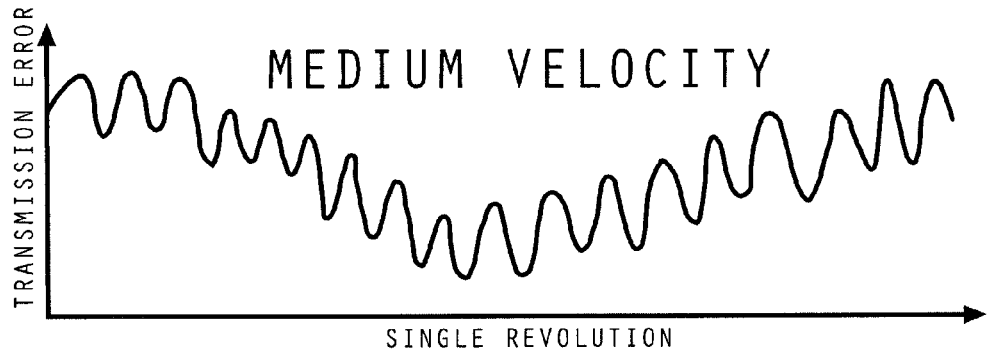
Figure 7C:
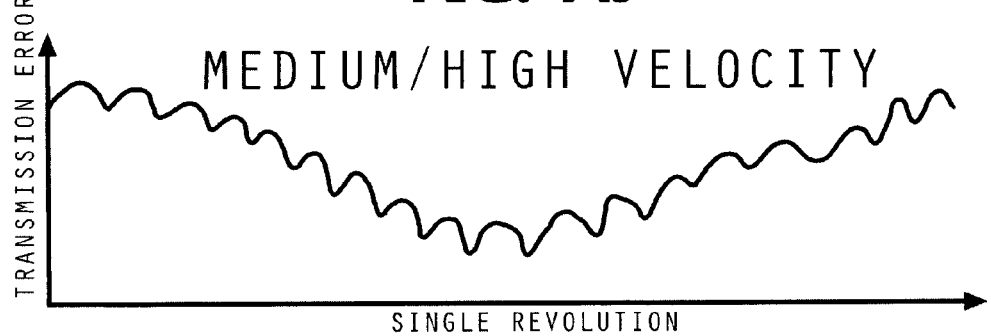
Figure 7D:
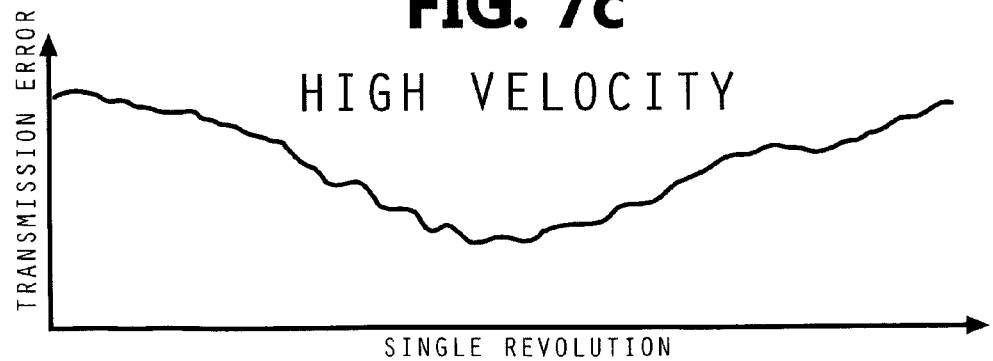

FIGS. 6b and 6c show an upper view (FIG. 6b) and a magnification of meshing cogwheels 902 and 906 (FIG. 6c) of a misaligned transmission gear system 900 that consequently causes transmission error. Shafts 904 and 908 in this example are not parallel. It will be noted that misalignment of shafts may refer not only to the angle between the shafts, as shown in FIGS. 6a-6c, but also to the distance/space between the shafts. In some embodiments, gear teeth geometry (e.g., involute teeth) and/or dimensions dictate the required spacing (i.e., accurate spacing) between the gear shafts (i.e., between the rotation axis of the gears) to ensure continuous and accurate angular movement of the gears. If the shafts are positioned too close to one another or too far from one another, this may lead to improper meshing of the respective gear teeth, resulting in transmission error.

In addition to misalignment of shafts, which may be a result of assembly errors and/or of forces applied on the shafts/gears, transmission error may be a consequence of the following:

Faulty bearings—an imperfect interface between a shaft and its bearing/s may result in eccentricity/wobbling of the shaft. For example, in the device shown in FIGS. 2a-2b, an imperfect interface between the rotating sleeve 160 and the casing 40 may lead to eccentricity/wobbling of the rotating sleeve 160 within the casing 40; and/or Faulty gear teeth—teeth not equally distributed along the circumference of a gear, teeth having different length and shape, etc.; and/or Faulty shaft/s—deformed shaft/s (e.g., curved), etc.

FIGS. 7a-7d show representative graphs of transmission error at various rotational velocities. The X axis represents a single revolution (cycle) of the output shaft/gear and the Y axis is the transmission error. In some embodiments, the low frequency wave ("carrier wave") is at a frequency of one wave per cycle of the output shaft. This low frequency transmission error may represent eccentricity of the output shaft, which may be a consequence of a faulty interface between the output shaft and its bearing/s, for example. The high frequency wave/s may be related to faulty gear teeth, for example. It can be seen that at high velocities the high frequency waves are diminished (i.e., their amplitude significantly decreases) because the effect of damaged teeth, for example, is relatively negligible.

Figure 8A:
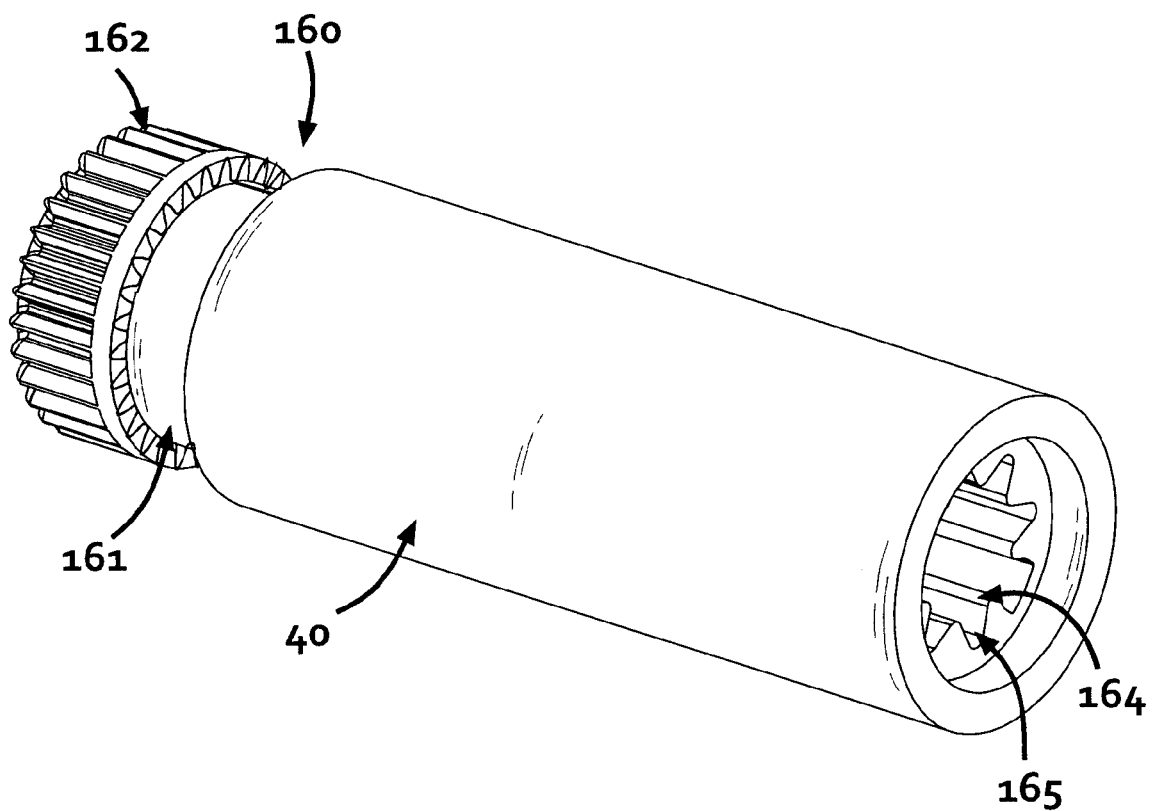
FIGS. 8a-8b shows a perspective view (FIG. 8a) and a transverse cross sectional view (FIG. 8b) of a rotating sleeve within a tube-shaped casing, according to some embodiments.
Figure 8B:
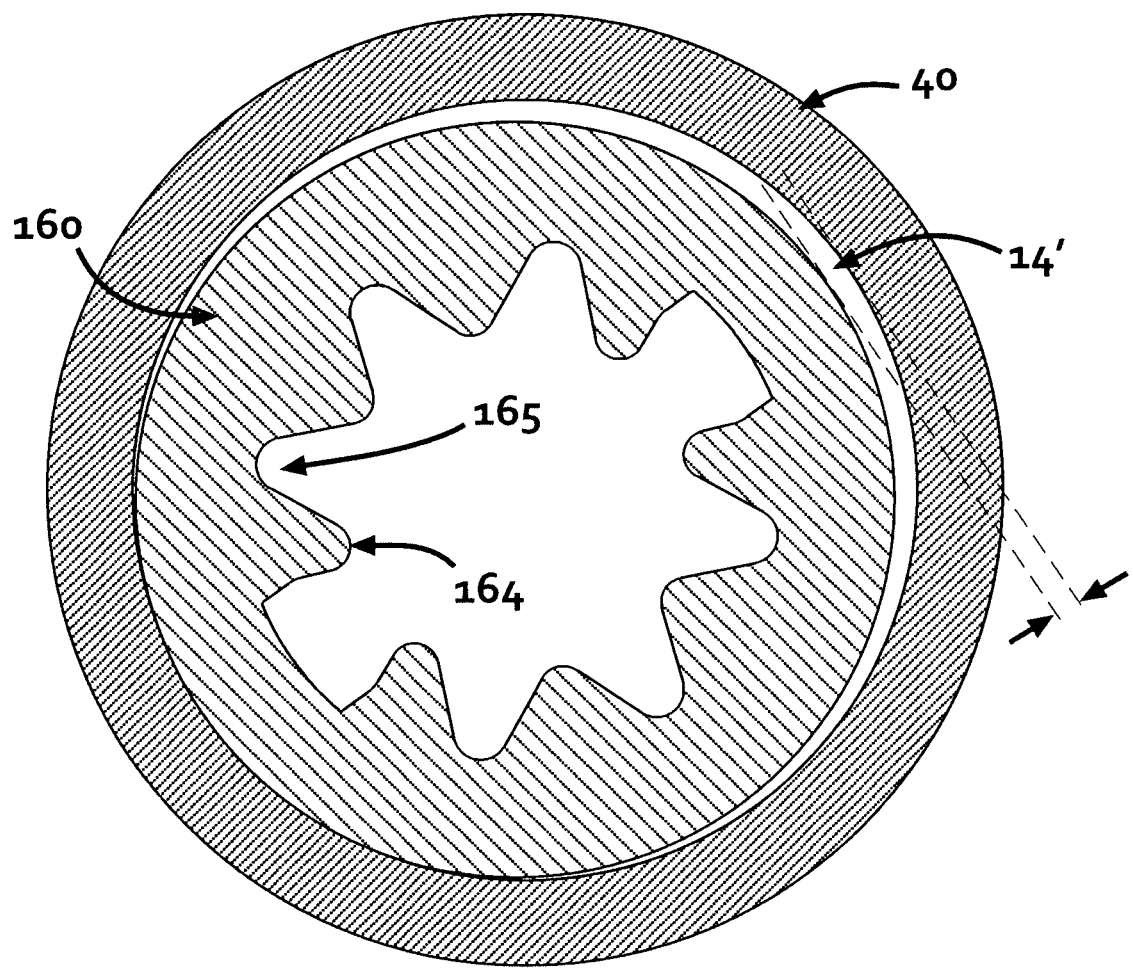

FIGS. 8a-8b show a perspective view (FIG. 8a) and a transverse cross sectional view (FIG. 8b) of the rotating sleeve 160, according to some embodiments. The sleeve 160 may be configured as an elongated substantially hollow shaft (e.g., cylindrical) 161 with a gear 162 at its proximal end. The inner part of the sleeve 160 may include longitudinal teeth (ridges) 164 occupying, in some embodiments, the entire length of the sleeve 160. In some embodiments, the longitudinal teeth 164 define longitudinal grooves 165 for receiving the drive-screw rotator 232. In some embodiments, the gear 162 is meshed with gear 134 (shown, for example, in FIG. 15) and is the last stage of the reduction gear system. The inner teeth 164 may engage with the drive-screw rotator 232 (shown, for example, in FIG. 3) upon connection of the reusable and disposable parts (shown, for example, in FIG. 3). In some embodiments, the rotating sleeve 160 (or at least a portion of its shaft 161) may be positioned within a sleeve housing/casing 40. The sleeve housing 40 may be configured as a tube, as shown in FIG. 8a. In some embodiments, the sleeve housing 40 may be configured as two (or more) supports (not shown) located at the two shaft ends, for example. These two or more supports may have a substantially annular configuration or any other configuration suitable for supporting the shaft 161. FIG. 8b shows the rotating sleeve 160 within the sleeve housing 40. A space 14' may be present between the rotating sleeve 160 and the sleeve housing 40 as a result of predetermined tolerances to enable free rotation of the sleeve 160 within the housing 40 (according to some embodiments), and/or as a result of undesired manufacturing tolerances of the sleeve 160 and/or of the casing 40. This space 14' may allow undesired wobbling motion of the sleeve 160 within the casing 40 resulting in eccentricity of the rotating sleeve 160 and variable friction forces between the sleeve 160 and the casing 40.

Figure 9:
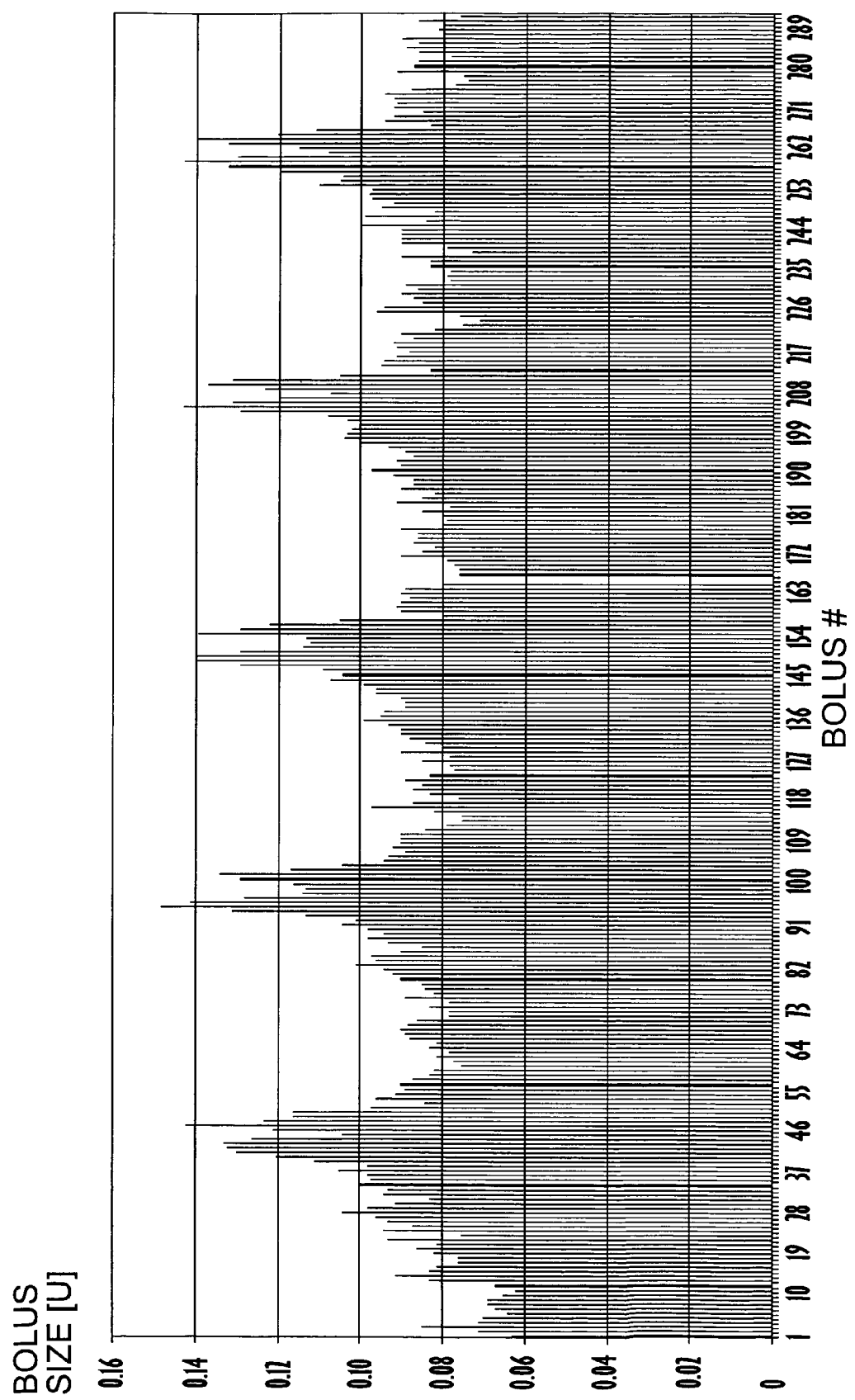
FIG. 9 shows a typical bar graph of consecutive bolus deliveries when transmission error exists, according to some embodiments.

FIG. 9 shows an example bar graph of consecutive bolus deliveries of a dispensing unit having a rotating sleeve, when transmission error exists. The X axis represents the number of bolus deliveries, and the Y axis represents the bolus size (in insulin units). In this example, each initiated bolus delivery should have resulted in the delivery of 0.1 U of insulin. However, the presence of transmission error/s leads to variability in the delivered insulin amounts, characterized by a low frequency sine wave as well as high frequency sine wave/s. In this example, the frequency of the low frequency sine wave corresponds to one full rotating sleeve rotation cycle. Thus, this sine wave may be the consequence of a transmission error related to the rotating sleeve and/or its interfaces with other components (e.g., gear 134 and/or the drive-screw rotator 232 in FIG. 2). In some embodiments, rotation of the rotating sleeve rotates the drive-screw rotator and thus the drive-screw, and the rotation of the drive-screw is consequently converted to linear motion of the drive-screw and the plunger within the reservoir, e.g., due to engagement of the drive-screw with a non-rotating nut. Thus, transmission errors related to the rotating sleeve, e.g., imperfect interface between the rotating sleeve and its casing (e.g., a tube-like casing, as shown in FIG. 8a) and/or imperfect interface between the drive-screw rotator and the rotating sleeve, may cause variations in the rotation of the drive-screw leading to variations in the linear movement of the piston, and consequently to cyclic variations in delivered bolus amounts corresponding to the rotating sleeve's cycle.

Figure 10A:
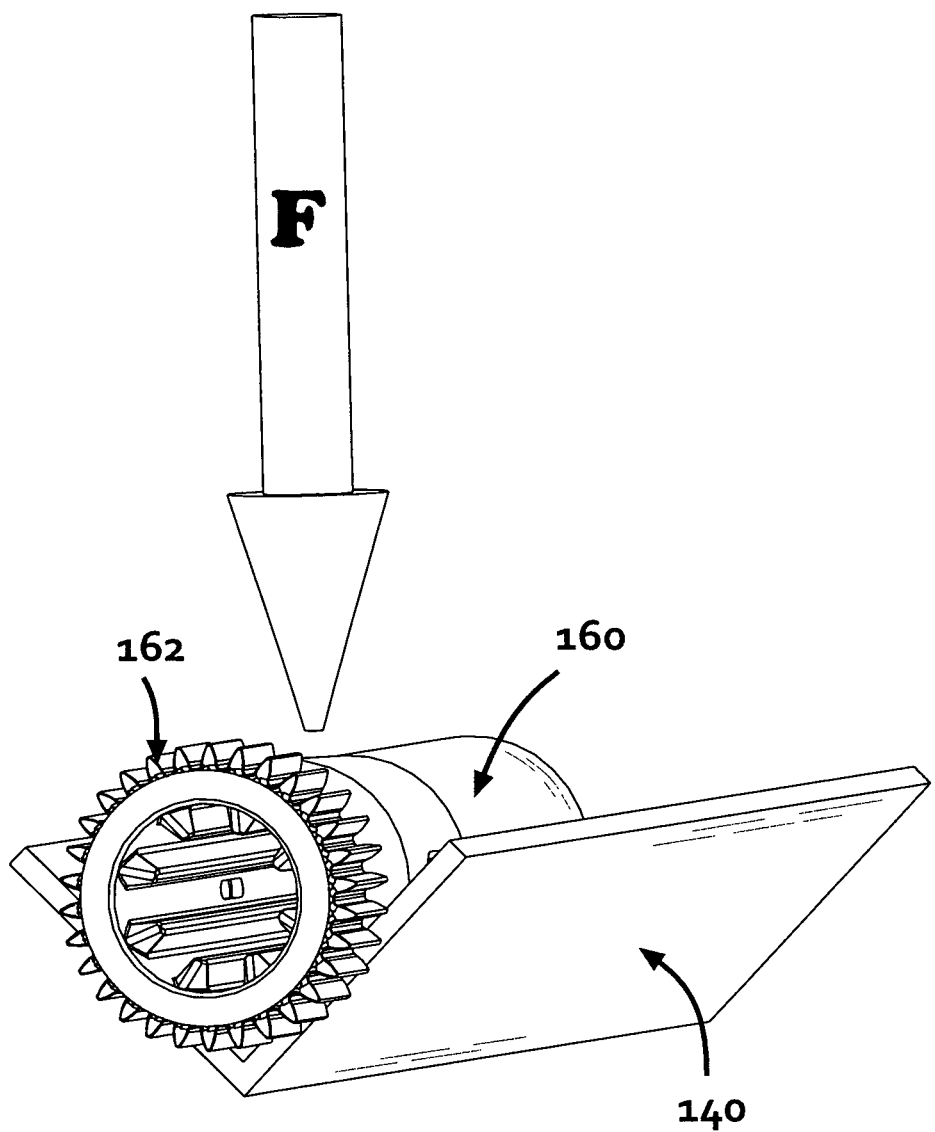
FIGS. 10a-10b show a perspective view (FIG. 10a) and a transverse cross sectional view (FIG. 10b) of a rotating sleeve aligned with a V-block casing by an applied external force, according to some embodiments.
Figure 10B:
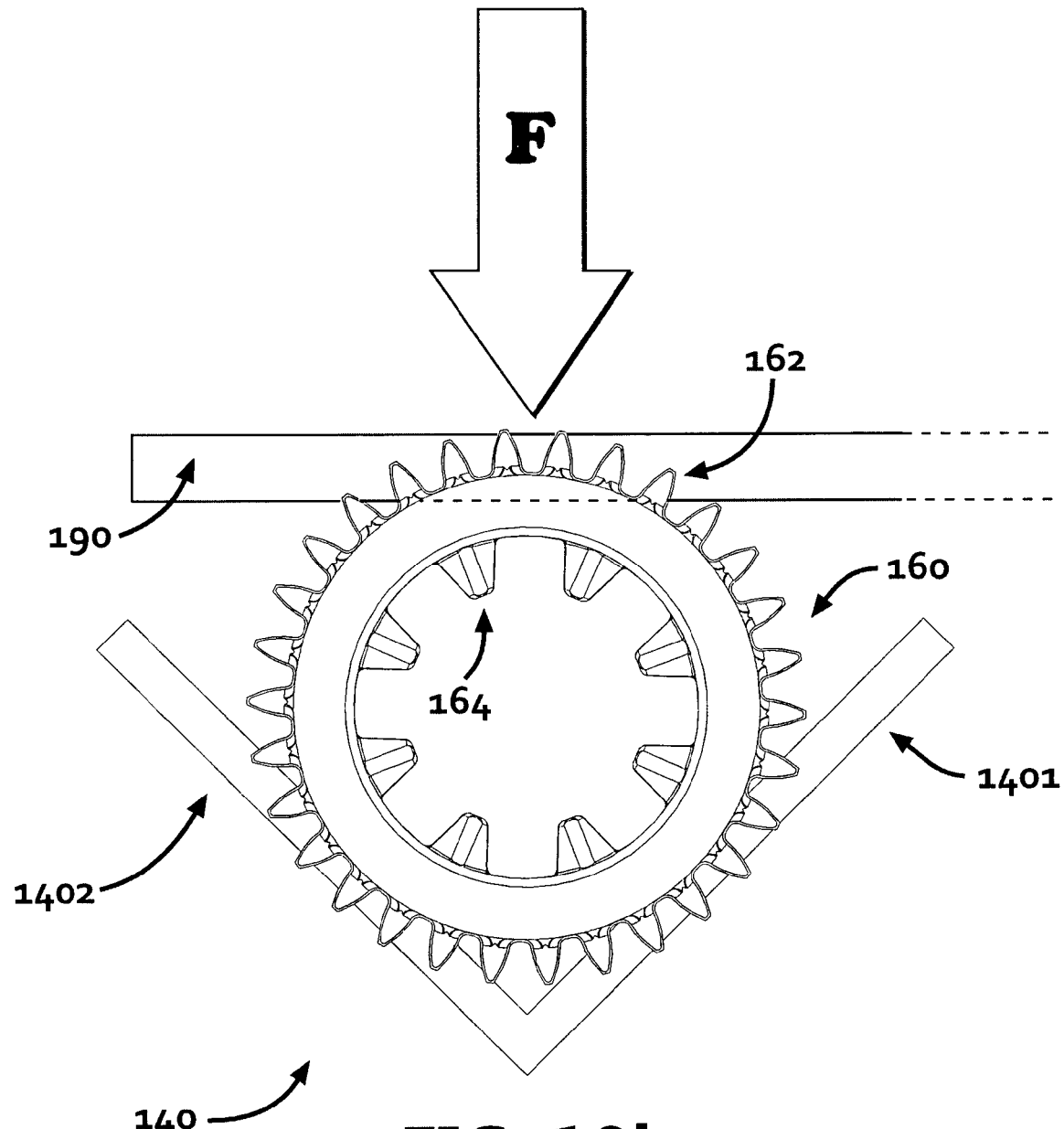
Figure 10C:
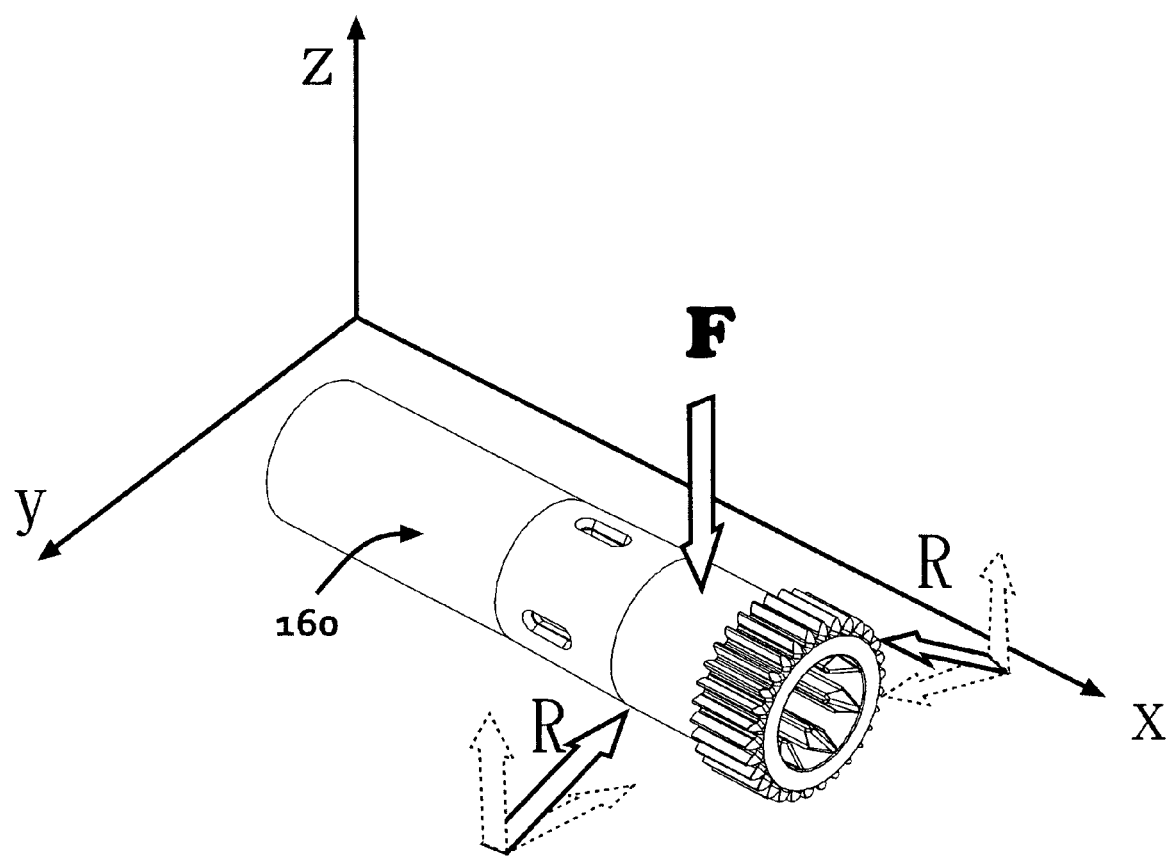
FIG. 10c shows the radial forces (R) acting on the rotating sleeve by the V-Block and the external force (F) that is applied by a spring to maintain constant alignment with the X axis, according to some embodiments.

FIGS. 10a-10b show a perspective view (FIG. 10a) and a transverse cross sectional view (FIG. 10b) of an embodiment of a rotating sleeve casing 140, which is configured (for example) as a V-block. The rotating sleeve 160 may be aligned with the V-block casing 140 by an applied external force (F). In some embodiments, the V-block/section includes at least a pair of walls having corresponding surfaces provided at an angle to one another thereby establishing a "trough" for holding the rotating sleeve. In some embodiments, the angle may be less than 180 degrees, and in some embodiments the angle may be less then 120 degrees. In some embodiments, the angle may be between 30 and 120 degrees, e.g., 90 degrees. In addition, according to some embodiments, the V-block, and corresponding surfaces, may be divided into a plurality of V-blocks/surfaces (e.g., two, three), which may be distributed such that the combined blocks/surfaces support a substantial portion of the length of the rotating sleeve. When the rotating sleeve 160 is forced against the walls of the V-shaped casing 140, there is little, and in some embodiments, no wobbling motion of the rotating sleeve 160 within the casing 140, thus the friction forces between the rotating sleeve 160 and the casing 140 are maintained substantially constant and stable. Further, the longitudinal axis of the rotating sleeve 160 is maintained aligned (angle and distance) with the longitudinal axis (e.g., rotation axis) of engaging gears (e.g., gear 134 shown in FIG. 11), with undesired manufacturing tolerances of the rotating sleeve 160 (e.g., slightly smaller/larger diameter) having minimal, and in some embodiments negligible, effect. FIG. 10b shows the rotating sleeve 160, the gear 162 at its proximal end, and the inner teeth 164. An external force (arrow) may be applied in this example by a biasing member, for example spring 190, that, in some embodiments, forces/biases (e.g., presses) the sleeve 160 against walls 1401 and 1402 of the V-block casing 140 (hereinafter in some embodiments referred to as the "spring loaded mechanism"). FIG. 10c shows the counter radial forces (R) acting on the rotating sleeve 160 by the walls of the V-shaped casing 140 and the external force (F) that is applied by the spring 190, for example, to maintain constant alignment of the rotating sleeve 160 with the X axis (corresponding to the longitudinal axis of the patch unit, for example).

Figure 11:
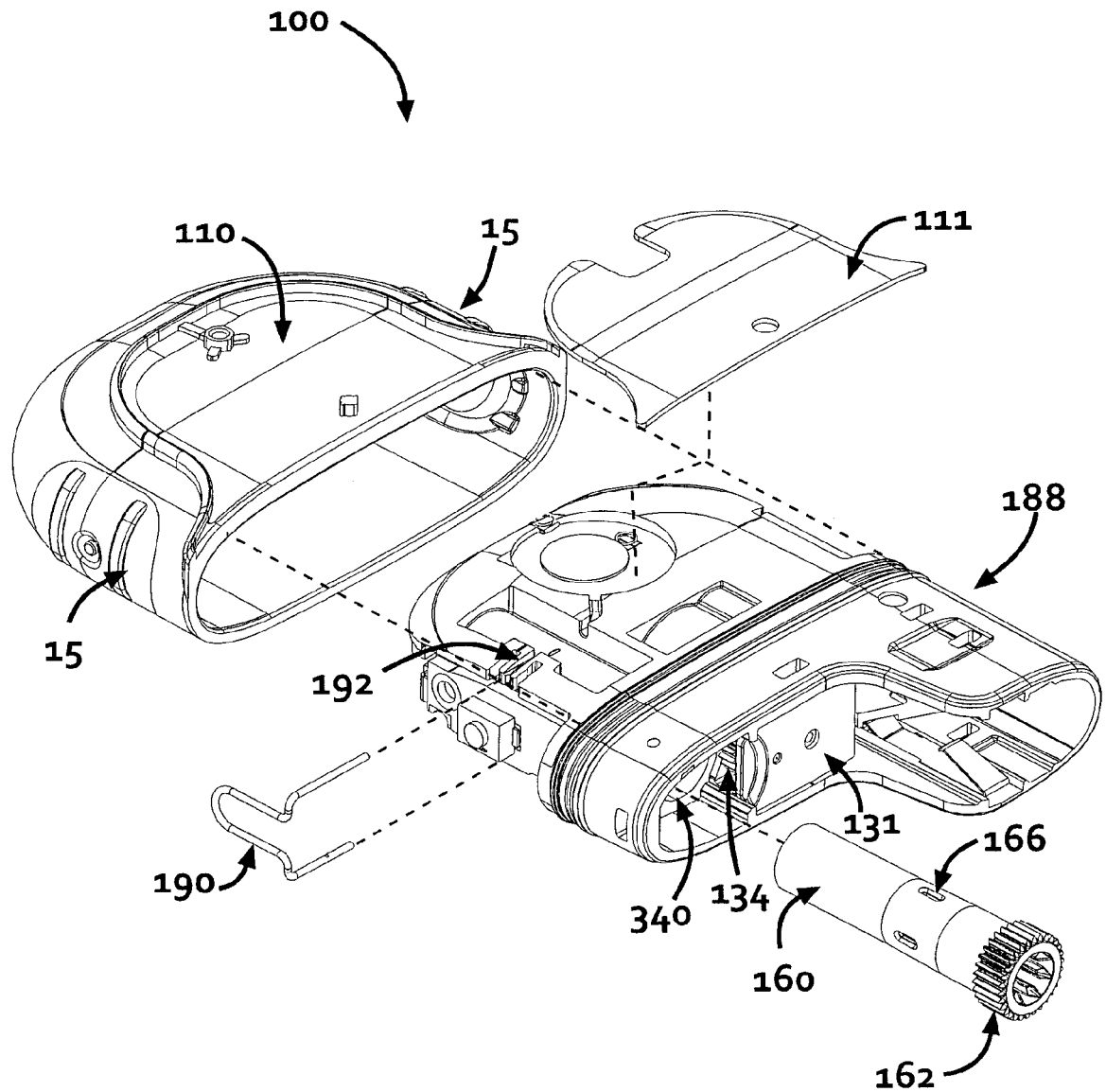
FIG. 11 shows a partial exploded view of a reusable part including a shell, chassis, rotating sleeve and supporting spring, according to some embodiments.

FIG. 11 shows a partial exploded view of an example reusable part 100. Shown are reusable part components, including the shell 110, chassis 188, rotating sleeve 160 and supporting spring 190. Two operating buttons/switches (e.g., bolus buttons) 15 may be positioned one on each side of the shell 110 and a protective shield 111 may be connected to the shell's upper side, according to some embodiments. The insert 188 may support one or more of: electronics, motor (not shown), gearbox 131, and the rotating sleeve 160 with the rotating sleeve gear 162. The rotating sleeve 160 may be supported by a casing 340, which may be either coupled to the chassis 188 or integral with the chassis 188. In some embodiments, the casing 340 includes at least one V-block section, and the rotating sleeve 160 is forced against the V-block walls/surfaces (not shown in FIG. 11) by spring 190. The spring 190 may be positioned within one or more slots, e.g., slot 192, in the chassis 188 and/or in the casing 340. In some embodiments, the rotating sleeve 160 may include at least one opening 166, to allow monitoring of the position of the drive-screw and/or the drive-screw rotator (both not shown in FIG. 11) within the rotating sleeve 160, in order to provide an "end of reservoir alert", as disclosed, for example, in International Patent Application Publication No. WO/2009/125398. In case the sleeve casing 340 surrounds the entire length of the sleeve 160 (e.g., a tube-shaped casing), or at least the portion of the sleeve 160 having the at least one opening 166, the casing 340 may include at least one opening (not shown in FIG. 11) corresponding to the at least one opening 166 of the sleeve 160. In some embodiments, the spring 190 may be a separate piece made of bent metal or plastic. In some embodiments, the spring 190 may be a flexible extension of the insert 188 and/or the casing 340 (e.g., molded as one part with the insert 188 and/or the casing 340).

Figure 12A:
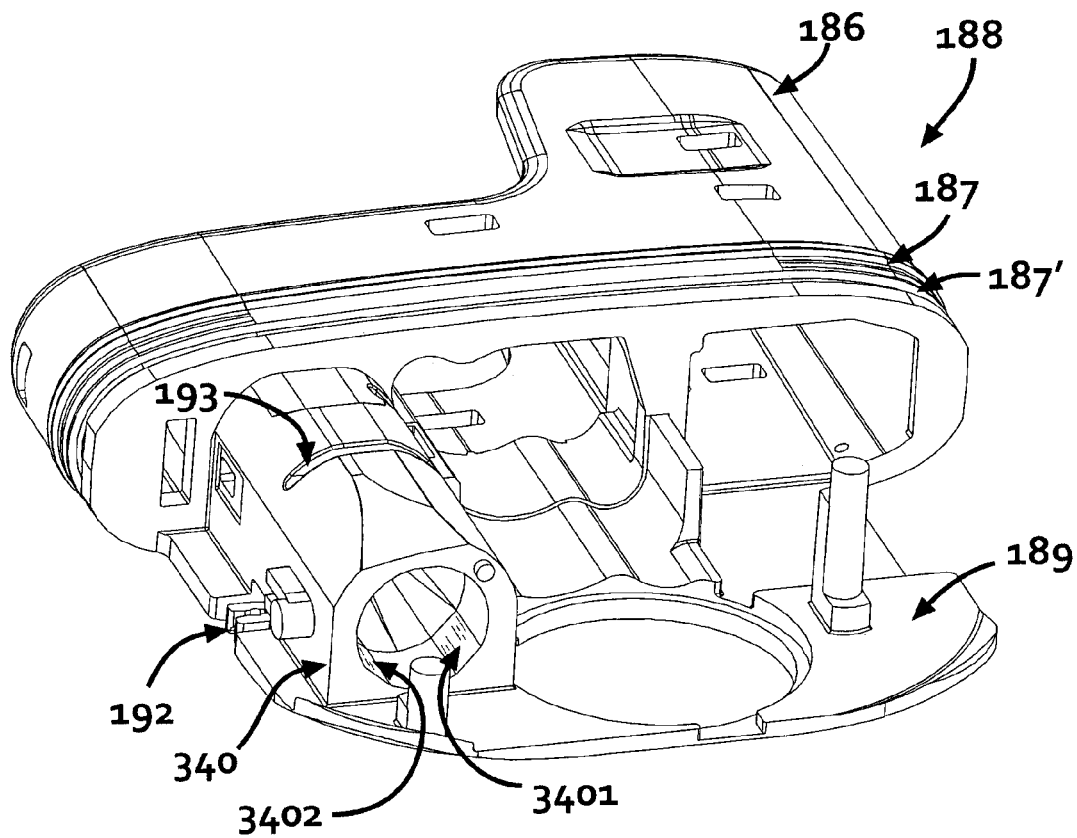
FIGS. 12a-12b show perspective views of the reusable part chassis before (FIG. 12a) and after (FIG. 12b) assembly of the rotating sleeve and supporting spring, according to some embodiments.
Figure 12B:
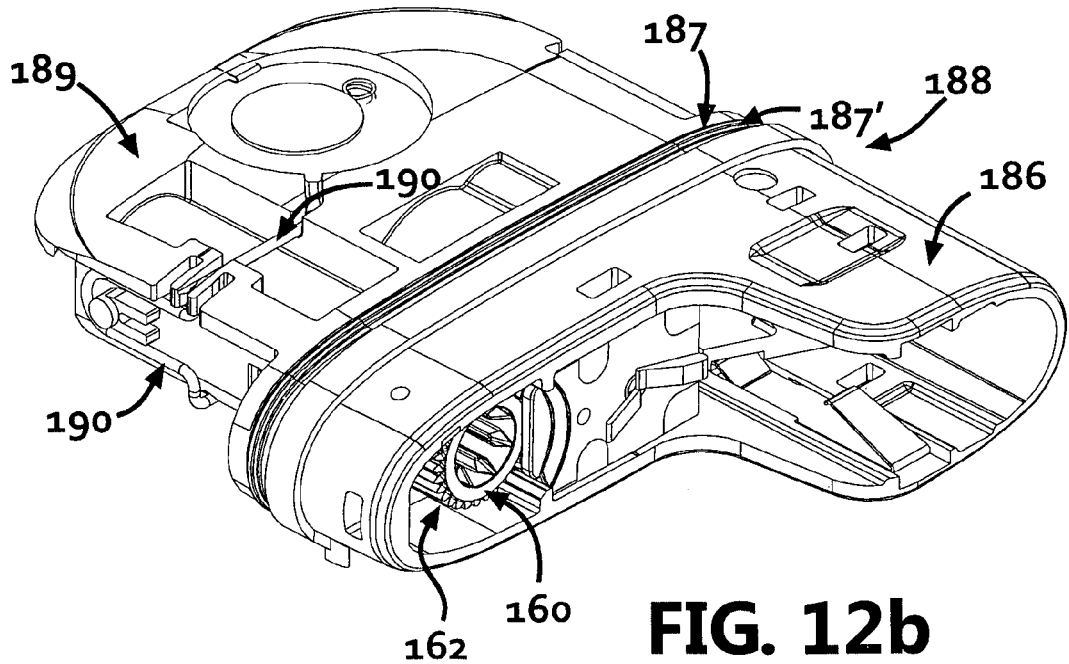

FIGS. 12a-12b show perspective views of the reusable part chassis (insert) 188 before (FIG. 12a) and after (FIG. 12b) assembly of the rotating sleeve 160 and the supporting spring 190 within the chassis 188, according to some embodiments. The chassis 188 may include a distal end 186 configured to be connected to the DP shell (not shown) and a proximal end 189 configured to support one or more or all of the electronics, buzzer, motor, gear, sensor, and capacitor, and to be received by the RP shell (not shown in FIGS. 12a-12b). One or more gaskets, e.g., gaskets 187 and 187', may be connected/coupled to the chassis 188 to maintain sealing with both the RP shell and the DP shell, respectively. These gaskets 187 and 187' may be glued to the chassis 188 or over-molded after, chassis molding. A portion of the chassis 188 may serve as the rotating sleeve casing 340 (i.e., the chassis 188 and the casing 340 may be manufactured as a single part). The casing 340 may include a pair of substantially flat walls/surfaces 3401 and 3402, which are provided at an angle relative to one another so as to form together (or function as) a V-block/section (or "V-groove"). In some embodiments, the angle between the two walls/surfaces 3401 and 3402 (which is equal to the angle between the perpendiculars to the walls/surfaces) may be less than 180 degrees, and in some embodiments the angle may be less then 120 degrees. In some embodiments, the angle may be between 30 and 120 degrees, e.g., 90 degrees. In some embodiments, the walls/surfaces 3401 and 3402 may be the contact areas between the rotating sleeve 160 and the casing 340. As noted above, in some embodiments, the casing 340 may include two or more V-blocks/sections (e.g., front and rear of the casing 340). The casing 340 and/or the chassis 188 may include slots, e.g., a lower slot 192 and an upper slot 193 to receive and fixate the supporting spring 190. At least one slot, e.g., slot 193, may be configured to allow access of the spring 190 to the rotating sleeve 160, so that the spring 190 may apply force on the rotating sleeve 160 against the V-block/s (spring loaded mechanism). In some embodiments, the force applied on the rotating sleeve gear 162 by an engaging gear (e.g., gear 134 shown in FIG. 11) may also be utilized for pressing the rotating sleeve 160 against the V-block/s.

Figure 13B:
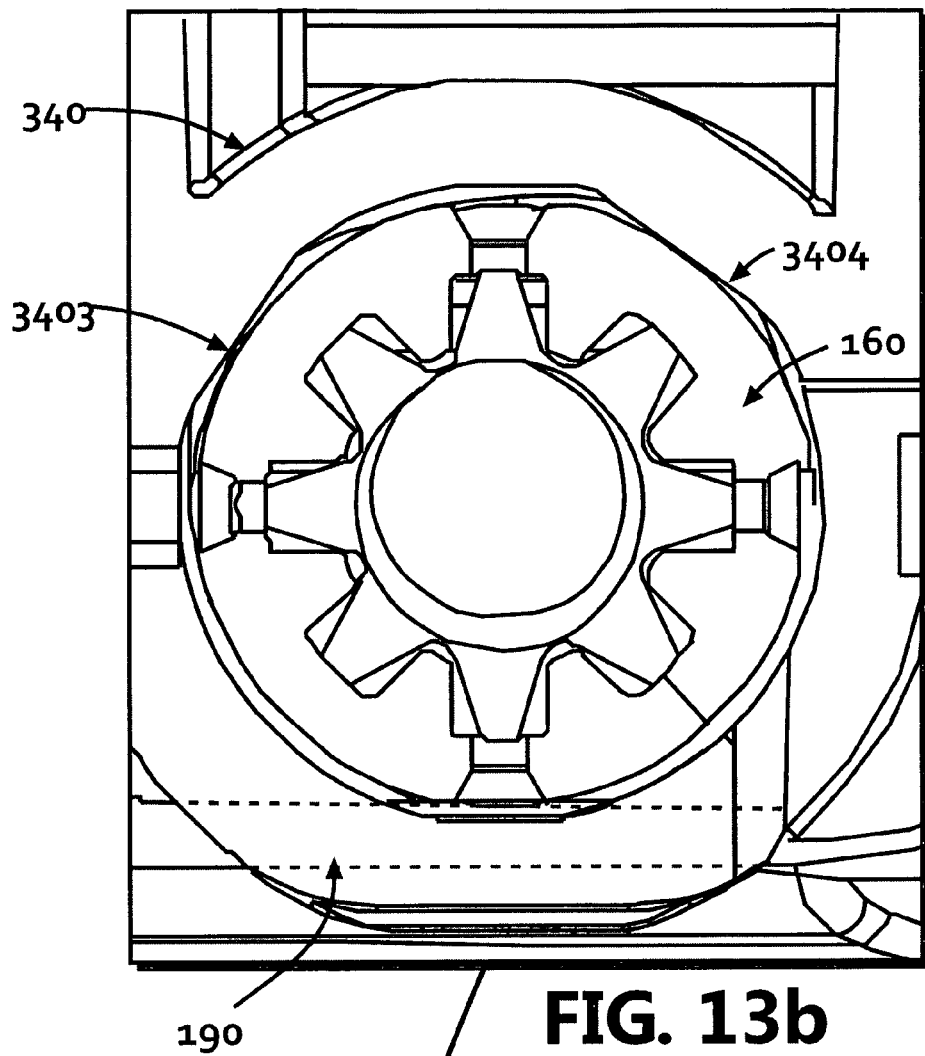
FIGS. 13a-13b show a transverse cross sectional view of the reusable part (FIG. 13a) and a magnified view of the rotating sleeve (FIG. 13b) including the supporting spring, according to some embodiments.
Figure 13A:
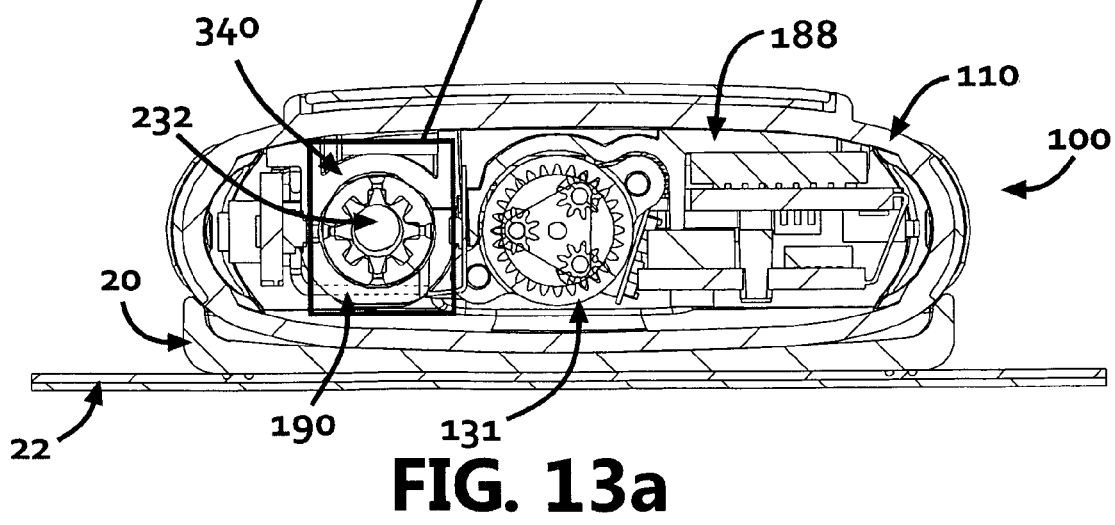

FIGS. 13a-13b show a transverse cross sectional view of the reusable part 100 (FIG. 13a) and a magnified view of the rotating sleeve 160 (FIG. 13b) including the supporting spring 190. The dispensing patch unit may be connected to a cradle 20 that is secured to the body (e.g., using an adhesive tape 22). The reusable part 100 may include a shell 110 and a chassis 188. The chassis 188 may support the gearbox 131 and other transmission/reduction gears (not shown). A portion of the chassis 188 may serve as the rotating sleeve casing 340 and may also be configured to receive and fixate the spring 190. According to some embodiments, the rotating sleeve 160 rotates within the casing 340 and is forced toward one or more V-blocks of the casing 340, e.g., the V-block composed of walls 3403 and 3404, by the spring 190, which penetrates the casing 340 through a dedicated slot (e.g., the slot designated by numeral 193 in FIG. 12a). The portion of the spring 190 which penetrates the casing 340 is shown in phantom lines in FIGS. 13a-13b. Further shown in FIGS. 13a and 13b is the positioning of the drive-screw rotator 232 within the rotating sleeve 160 when the DP 200 is connected to the RP 100.

Figure 14A:
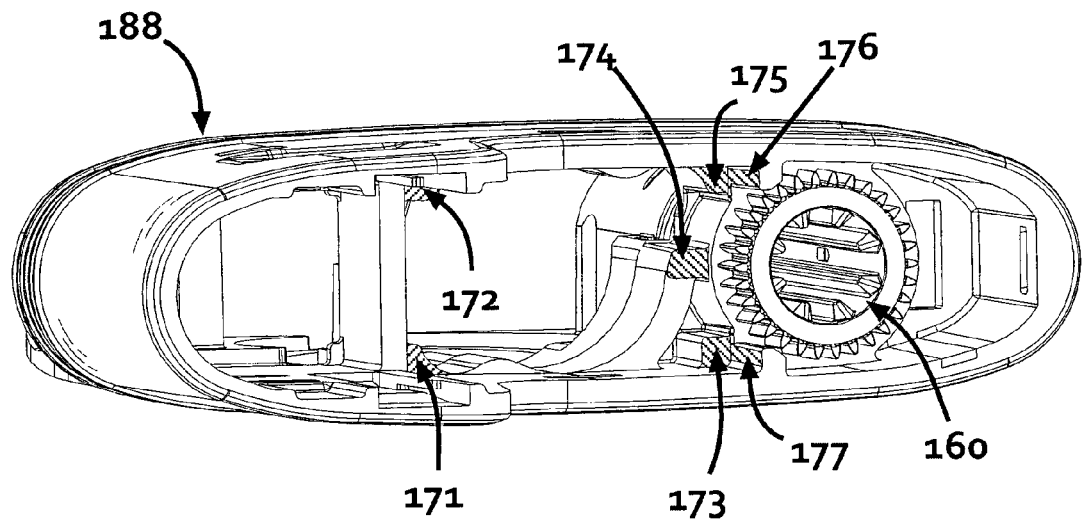
FIGS. 14a-14b show perspective views of the reusable part chassis including the alignment surfaces before (FIG. 14a) and after (FIG. 14b) assembly of the planetary gear and the motor, according to some embodiments.
Figure 14B:
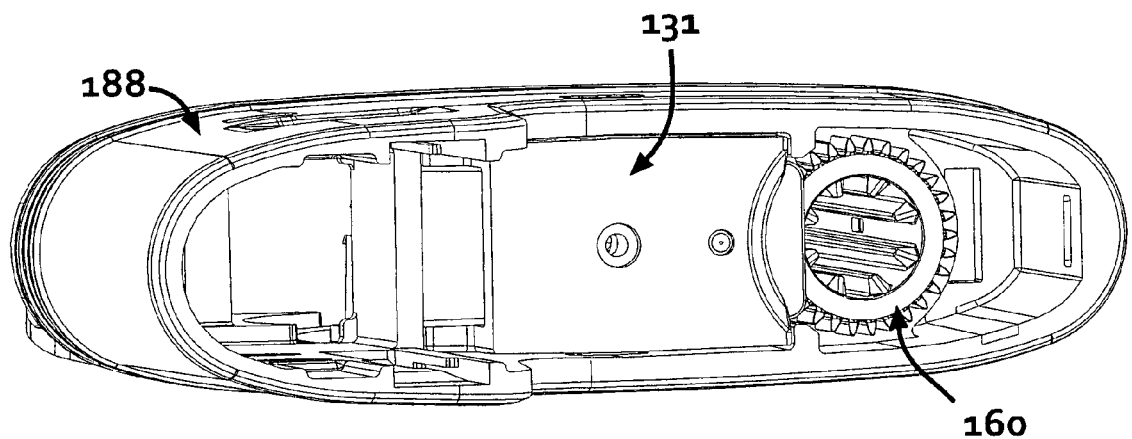

FIG. 14a shows a perspective view of the RP chassis (insert) 188 before assembly of the motor and the gearbox, according to some embodiments, and with the rotating sleeve 160 in place. The chassis 188 may include multiple alignment surfaces 171, 172, 173, 174, 175, 176, 177 to maintain parallel alignment (or at least substantially so) and accurate spacing (or at least substantially so) between the longitudinal axis (or rotation axis) of the motor and gearbox 131 (not shown in FIG. 14a) and the longitudinal axis (or rotation axis) of the rotating sleeve 160, or at least between the longitudinal axis (or rotation axis) of gear 134 (not shown in FIG. 14a) and the longitudinal axis (or rotation axis) of the rotating sleeve 160. In some embodiments, the gearbox 131 may be pressed against one or more of the alignment surfaces 171-177 using latches/snaps and/or an adhesive. In some embodiments, the shell/casing of the gearbox 131 may include at least one relatively elastic portion (e.g., a crush rib) which, when pressed against the chassis 188, presses the gearbox 131 against one or more of the alignment surfaces 171-177. FIG. 14b shows the RP chassis 188 after assembly of the motor (not shown in FIG. 14b) and the gearbox 131, in addition to the rotating sleeve gear 160.

Figure 15:
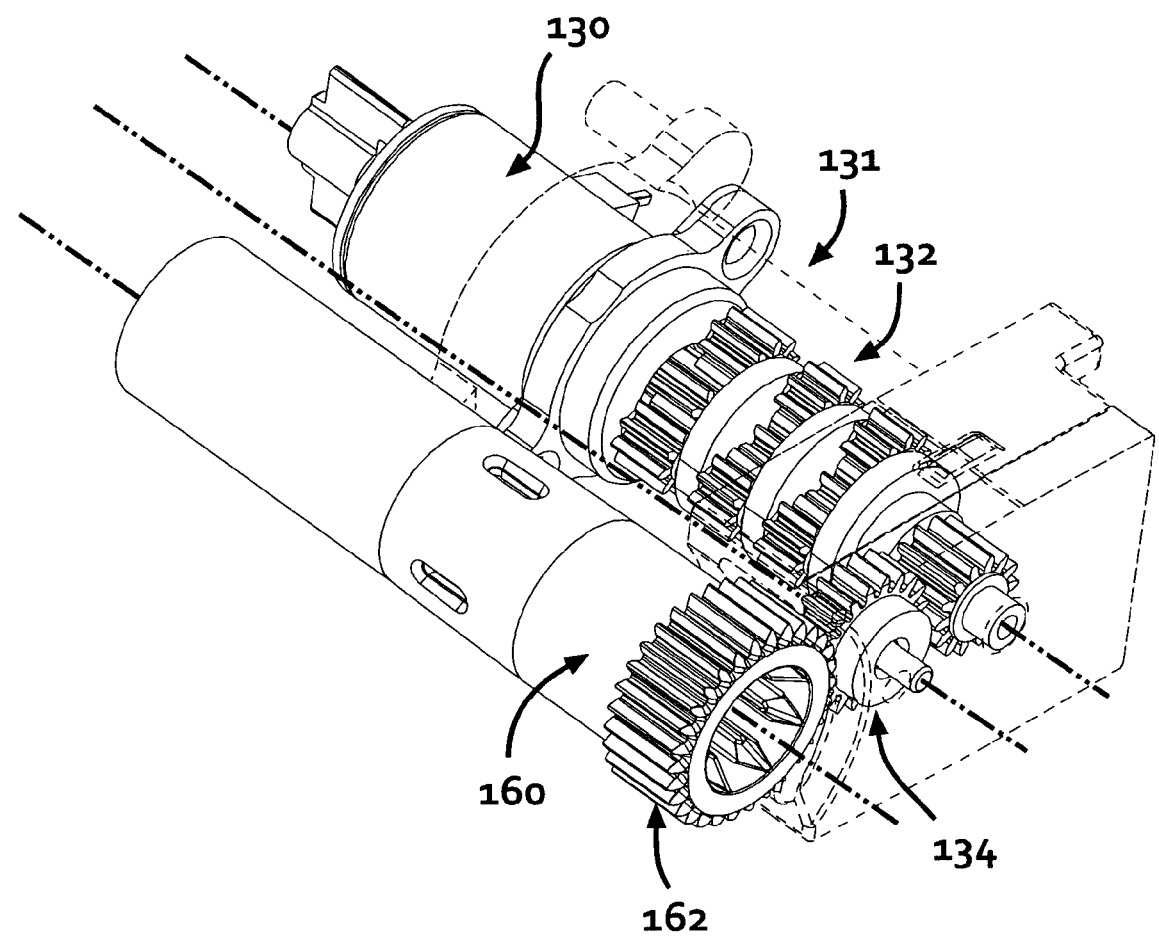
FIG. 15 shows the motor and planetary gear parallel aligned with the rotating sleeve and the rotating sleeve gear, according to some embodiments.

FIG. 15 shows an example driving mechanism of a patch unit, according to some embodiments, including the motor 130, the gearbox 131, and the rotating sleeve 160 with its gear 162. In some embodiments, the gearbox 131 may comprise a planetary unit 132 and one or more additional gears 134 (e.g., reduction gear/s, idler gear/s) between the rotating sleeve gear 162 and the planetary unit 132. The longitudinal axis (rotation axis) of the rotating sleeve 160 and its gear 162 is parallel aligned (or at least substantially so) with the longitudinal axis (rotation axis) of the motor 130 and the planetary unit 132 and with the longitudinal axis (rotation axis) of the gear 134.

Figure 16:
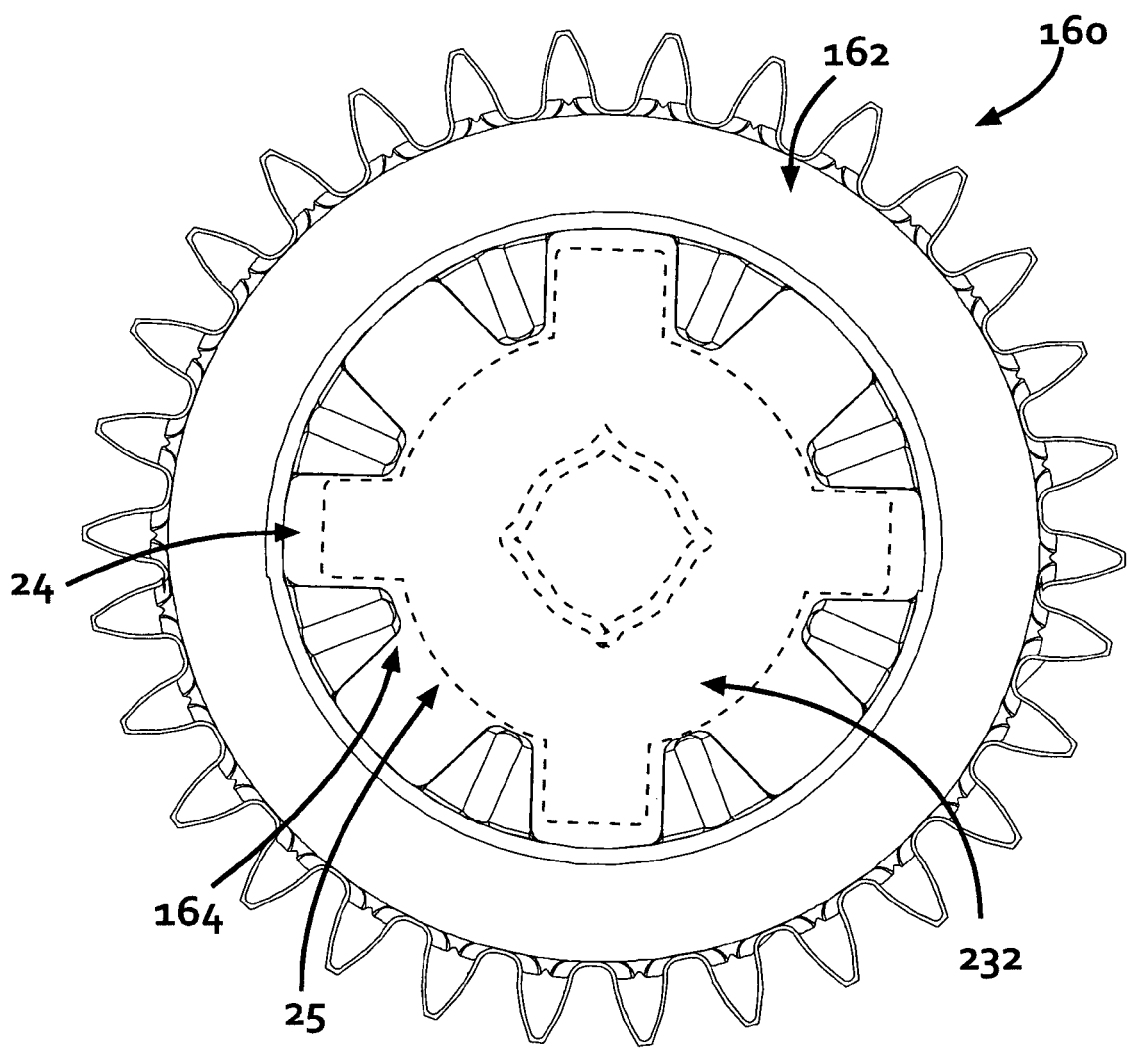
FIG. 16 shows a transverse cross sectional view of the rotating sleeve and the drive-screw rotator, according to some embodiments.

FIG. 16 shows a transverse cross sectional view of the rotating sleeve 160 and a drive-screw rotator 232 positioned therein. The drive-screw rotator 232 may include a varying number of teeth (ridges), e.g., four teeth 24. The teeth 24 of the drive-screw rotator 232 engage with the teeth 164 of the rotating sleeve 160 such that rotation of the sleeve 160 rotates the drive-screw rotator 232, and thus the drive-screw (not shown in FIG. 16), since the drive-screw rotator 232 is either integral with the drive-screw or rigidly attached to the drivescrew. It will be noted that the drive-screw rotator 232 does not rotate relative to the sleeve 160. Unlike the interaction between two engaging gears, where rotation of one gear causes the other gear to rotate in the opposite direction as a result of meshing of the gear teeth, engagement of the drive-screw rotator teeth 24 with the sleeve teeth 164 causes the drive-screw rotator 232, and thus the drive-screw 230, to rotate together with the sleeve 160, in the same direction. The sleeve teeth 164 "push/pull" the rotator teeth 24 along with them as they rotate, allowing only linear relative movement between the drive-screw rotator 232 and the sleeve 160. As shown in FIG. 16, the drive-screw rotator 232 may include surfaces 25 ("centralizing surfaces") between adjacent rotator teeth 24 for ensuring proper alignment between the rotator 232 and the sleeve 160 by maintaining contact with the upper portions of the sleeve teeth 164. Depending on the embodiment, each centralizing surface 25 may maintain contact with the upper portion of one or more teeth 164 of the rotating sleeve 160.

Figure 17C:
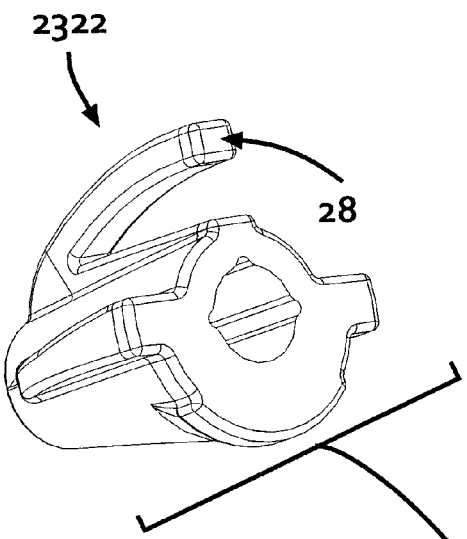
FIGS. 17a-17f show diagrams of various configurations of the drive-screw rotator, according to some embodiments.
Figure 17B:
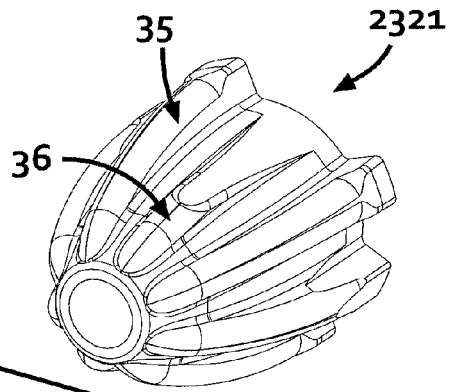
Figure 17D:
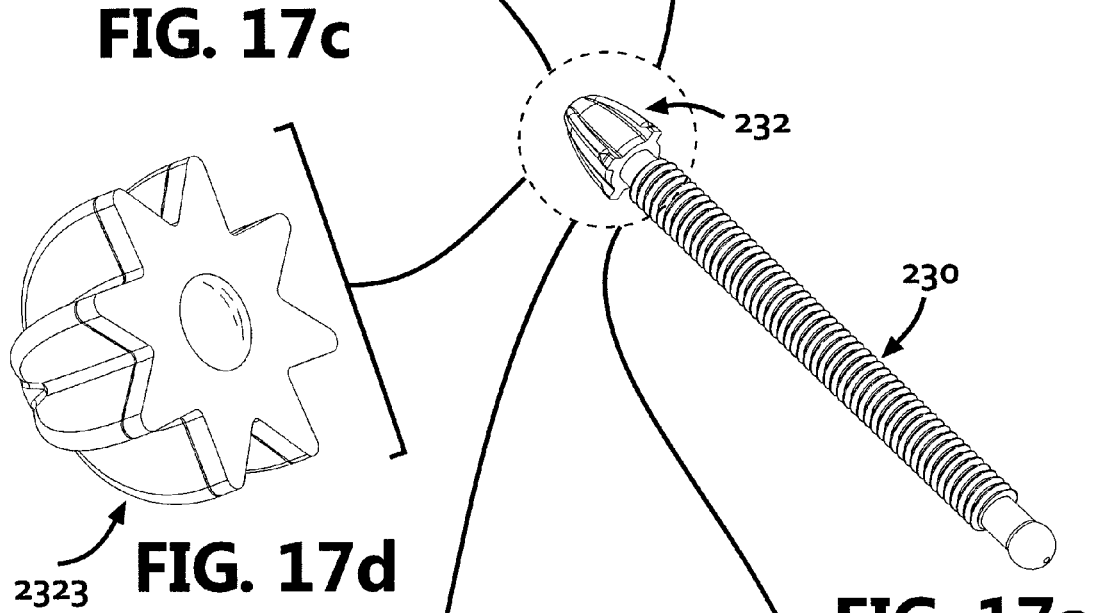
Figure 17A:
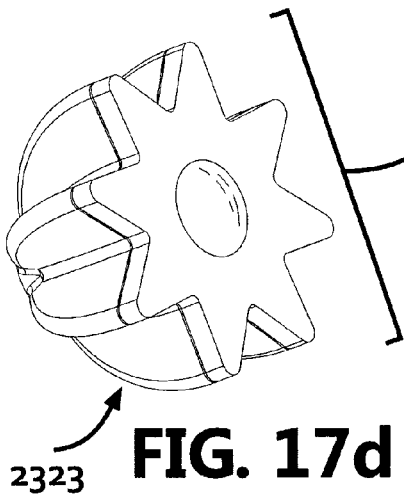
Figure 17E:
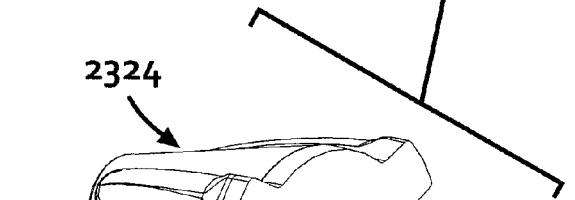
Figure 17F:
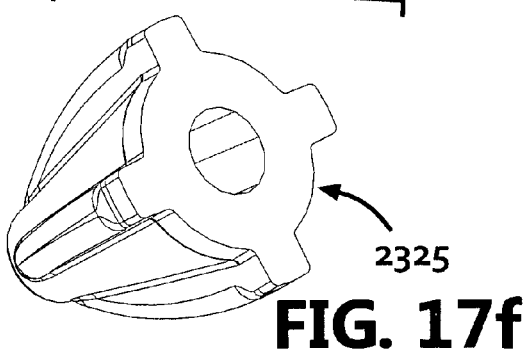

FIGS. 17a-17f show perspective views of the drive-screw 230 and various configurations of the drive-screw rotator 232, according to some embodiments. FIG. 17a shows the drive-screw 230 and the drive-screw rotator 232, which may be integral with the drive-screw 230 or attached (e.g., glued) to the drive-screw 230. FIG. 17b shows a rotator 2321 having a plurality of "full" teeth ("ridges") 35, which may extend from the tip of the drive-screw rotator 232 to its base, and one or more "partial" teeth 36, e.g., one "partial" tooth 36 between every two adjacent "full" teeth 35, which may stem from the tip of the drive-screw rotator 232, similar to the "full" teeth 35, but terminate before reaching the base of the rotator 232, according to some embodiments. The "full" teeth 35 may be used for both guiding the drive-screw rotator 2321 into the rotating sleeve (not shown in FIG. 17b) and engaging with the teeth of the rotating sleeve to enable rotation of the drive-screw upon rotation of the rotating sleeve. In some embodiments, the "partial" teeth 36 are used for guiding the drive-screw rotator 2321 into the rotating sleeve (i.e., to further facilitate the proper insertion of the drive-screw rotator 2321 into the rotating sleeve 160). In some embodiments, the "partial" teeth 36 do not engage with the teeth of the rotating sleeve so as to enable rotation of the drive-screw upon rotation of the rotating sleeve, because their small size and/or length prevents them from maintaining contact with the sleeve teeth. FIG. 17c shows a rotator 2322 having three teeth, where one tooth 28 is flexible to provide a spring mechanism such that when the rotator 2322 is inserted into the sleeve 160 the spring-like tooth 28 secures the rotator 2322 in place and prevents any undesired wobbling of the rotator 2322 within the sleeve 160, according to some embodiments. FIG. 17d shows a rotator 2323 having a plurality of teeth (e.g., eight) substantially evenly distributed along the circumference of the rotator 2323, according to some embodiments. FIG. 17e shows a rotator 2324 having three teeth, according to some embodiments. FIG. 17f shows a rotator 2325 having four teeth, according to some embodiments.

Any and all references to publications or other documents, including but not limited to, patents, patent applications, articles, books, etc., presented in the present application, are herein incorporated by reference in their entirety.

Although particular embodiments have been disclosed herein in detail, this has been done by way of example for purposes of illustration only, and is not intended to be limiting with respect to the scope of the embodiments of the present disclosure. In particular, it is contemplated that various substitutions, alterations, and modifications may be made without departing from the spirit and scope of any embodiment disclosed herein. Moreover, other aspects, advantages, and modifications are considered to be within the scope of the disclosed embodiments.

What is claimed is:

1. A fluid infusion device for delivering a drug into the body of a user, comprising:
   at least one housing;
   a reservoir for containing the drug;
   a plunger for displacing the drug from the reservoir to the user;
   a drive-screw including a first end and a second end, the first end being configured to operatively connect to the plunger;
   a driving mechanism comprising at least a motor and one or more gears, wherein the one or more gears include a rotating sleeve configured to engage with the second end of the drive-screw; and
   a support casing substantially contained within the housing, the casing comprising a tube configured to substantially support the rotating sleeve along at least a substantial portion of a length thereof, and enable substantially free rotation of the rotating sleeve within the tube of the casing;
   wherein an interior of the support casing comprises at least one pair of substantially flat surfaces positioned adjacent to one another, wherein the surfaces are positioned relative to one another at an angle less than 180 degrees, and a biasing member for biasing the rotating sleeve relative to the at least one pair of substantially flat surfaces.

2. The device according to claim 1, wherein the support casing is further configured to maintain a rotation axis of the rotating sleeve substantially parallel to a rotation axis of at least one other gear of the one or more gears.

3. The device according to claim 1, wherein the support casing is further configured to maintain the rotating sleeve and at least one other gear of the one or more gears in a substantially parallel alignment.

4. The device according to claim 3, wherein the support casing is further configured to maintain the rotating sleeve and at least one other gear of the one or more at gears at a spacing therebetween.

5. The device according to claim 1, further comprising a chassis for supporting at least a portion of the driving mechanism and the support casing.

6. The device according to claim 5, wherein the support casing is integral with the chassis.

7. The device according to claim 5, wherein the chassis includes a plurality of alignment surfaces configured to maintain at least one of substantially parallel alignment and substantially accurate spacing between at least two of a rotation axis of the motor, a rotation axis of the one or more gears and a rotation axis of the rotating sleeve.

8. The device according to claim 1, wherein the casing comprises an interior with a shape substantially corresponding to an exterior shape of the rotating sleeve.

9. The device according to claim 1, wherein the biasing member comprises a spring.

10. The device according to claims 1, wherein the rotating sleeve includes at least one opening to enable monitoring of the position of at least one of the drive-screw and the second end thereof within the rotating sleeve.

11. The device according to claim 1, wherein the second end of the drive-screw is integral with the drive-screw.

12. The device according to claim 1, wherein the rotating sleeve includes a plurality of internal grooves or teeth extending along at least a portion of the length of the rotating sleeve.

13. The device according to claim 12, wherein the second end of the drive-screw includes a plurality of teeth configured to engage with the internal grooves or teeth of the rotating sleeve.

14. The device according to claim 13, wherein the second end of the drive-screw further includes a plurality of centralizing surfaces between adjacent teeth, the plurality of centralizing surfaces being configured to substantially align the second end with the internal grooves or teeth of the rotating sleeve.

15. The device according to claim 1, wherein the rotating sleeve comprises a substantially cylindrical configuration.

16. The device according to claim 1, wherein the at least one housing comprises a first housing connectable to a second housing, the first housing being configured to house at least the support casing and at least a portion of the driving mechanism including the rotating sleeve, and the second housing being configured to house at least the reservoir, the plunger, and the drive-screw, and wherein upon connection between the first housing and the second housing the second end of the drivescrew is received within the rotating sleeve.

* * * * *